(12) United States Patent
Searchfield et al.

(10) Patent No.: US 9,808,715 B2
(45) Date of Patent: Nov. 7, 2017

(54) INTERACTIVE GAMING SYSTEM

(75) Inventors: Grant Donald Searchfield, Auckland (NZ); Kei Kobayashi, Waitakere (NZ); Kimberly Jane Wise, Auckland (NZ)

(73) Assignee: Auckland Uniservices Ltd., Auckland (NZ)

( * ) Notice: Subject to any disclaimer, the term of this patent is extended or adjusted under 35 U.S.C. 154(b) by 718 days.

(21) Appl. No.: 14/123,423

(22) PCT Filed: May 30, 2012

(86) PCT No.: PCT/NZ2012/000081
§ 371 (c)(1),
(2), (4) Date: Feb. 20, 2014

(87) PCT Pub. No.: WO2012/165978
PCT Pub. Date: Dec. 6, 2012

(65) Prior Publication Data
US 2014/0171195 A1 Jun. 19, 2014

(30) Foreign Application Priority Data
May 30, 2011 (NZ) ......................... 593160

(51) Int. Cl.
*A63F 13/00* (2014.01)
*A63F 13/424* (2014.01)
(Continued)

(52) U.S. Cl.
CPC ............ *A63F 13/424* (2014.09); *A61B 5/128* (2013.01); *A61B 5/4836* (2013.01);
(Continued)

(58) Field of Classification Search
CPC ........ H04R 25/70; H04R 25/75; A61B 5/125; A61B 5/4842; A61B 5/128; A61B 5/123
(Continued)

(56) References Cited

U.S. PATENT DOCUMENTS

| 2005/0192514 A1* | 9/2005 | Kearby | A61B 5/411 600/559 |
| 2006/0093997 A1* | 5/2006 | Kearby | G09B 21/009 434/185 |
| 2009/0124850 A1 | 5/2009 | Moore et al. | |
| 2009/0292221 A1 | 11/2009 | Viirre et al. | |

FOREIGN PATENT DOCUMENTS

WO  WO-2012/165978 A1  12/2012

OTHER PUBLICATIONS

"International Application Serial No. PCT/NZ2012/000081, International Preliminary Report on Patentability dated Dec. 2, 2013", 4 pgs.

(Continued)

*Primary Examiner* — Michael Cuff
(74) *Attorney, Agent, or Firm* — Schwegman Lundberg & Woessner, P.A.

(57) ABSTRACT

An interactive gaming system for a user suffering tinnitus. The system comprises a game machine configured to provide a game scenario in which the user's performance in the game scenario is based on the user's response to audio cue arrangements comprising a combination of sounds, and where at least one of the sounds has one or more sound characteristics, that are configured based on one or more sound characteristics of the user's perceived tinnitus. The system further comprises an audio delivery device or devices that are driven by the game machine to present the audio cue arrangements to the user in accordance with the game scenario and a user interface in signal communication with the game machine and which is operable by a user to interact with the game scenario by responding to the audio cue arrangements.

55 Claims, 15 Drawing Sheets

(51) Int. Cl.
*A63F 9/00* (2006.01)
*A63F 9/24* (2006.01)
*A61B 5/12* (2006.01)
*A61B 5/00* (2006.01)
*A61F 11/00* (2006.01)

(52) U.S. Cl.
CPC .............. *A63F 9/0001* (2013.01); *A63F 9/24* (2013.01); *A61F 11/00* (2013.01); *A63F 2009/0007* (2013.01); *A63F 2009/2402* (2013.01); *A63F 2009/247* (2013.01); *A63F 2009/2477* (2013.01); *A63F 2300/308* (2013.01); *A63F 2300/6081* (2013.01)

(58) Field of Classification Search
USPC .......................................................... 463/35
See application file for complete search history.

(56) References Cited

OTHER PUBLICATIONS

"International Application Serial No. PCT/NZ2012/000081, International Search Report dated Aug. 27, 2012", 4 pgs.
"International Application Serial No. PCT/NZ2012/000081, Written Opinion dated Aug. 27, 2012", 3 pgs.
Londero, Alain, et al., "Auditory and visual 3D virtual reality for chronic subjective tinnitus: theoretical framework", *Virtural Reality*, 14, (2010), 143-151.
Van Labeke, Nicolas, "Principled design of game-based auditory learning environments; Examples for Tinnitus", *IHR/NBRUH Science Meeting*, University of Nottingham, (Oct. 5, 2010), 16 pgs.

* cited by examiner

INTERACTIVE GAMING SYSTEM

PRIORITY CLAIM TO RELATED APPLICATIONS

This application is a U.S. National Stage Application under 35 U.S.C. §371 of PCT/NZ2012/000081, filed May 30, 2012, and published as WO 2012/165978 A1 on Dec. 6, 2012, which claims priority to New Zealand Application No. 593160, filed May 30, 2011, which applications and publication are incorporated by reference as if reproduced herein and made a part hereof in their entirety, and the benefit of priority of each of which is claimed herein.

FIELD OF THE INVENTION

The present invention relates to an interactive gaming system for auditory training rehabilitation relating to tinnitus.

BACKGROUND TO THE INVENTION

Tinnitus is the perception of sound in the absence of a corresponding external source. It can be perceived in one or both ears, or in the head, or outside the head. It is usually described as a ringing noise, but can also be in other forms such as hissing, buzzing, or roaring sounds. Tinnitus can be intermittent or it can be continuous and in such cases can be a cause of great distress to the sufferer.

Tinnitus is not a disease but a symptom resulting from a range of possible underlying causes including, for example, ear infections, foreign objects or wax in the ear, nose allergies, noise-related trauma, side effect of medication or other unexplained causes. Currently, there is no surgical cure for tinnitus. However, temporary relief for sufferers can be provided by external sound devices, for example masking instruments, as tinnitus sufferers often indicate that their tinnitus is less audible in the presence of other sounds.

Another approach to tinnitus management, is the recent trend toward using Tinnitus Retraining Therapy (TRT). TRT is a specific clinical method based on a neurophysiological model of tinnitus. The method is aimed at habituation of reactions evoked by tinnitus, and subsequently habituation of the tinnitus perception. Typically, the therapy involves counseling, aimed at reclassification of tinnitus to a category of a neutral signal, and sound therapy, aimed at weakening tinnitus-related neuronal activity. Effectively the TRT method is trying to retrain the patient's brain so that they treat their tinnitus similar to natural sounds that they can accommodate.

Most of the current TRT techniques are time consuming and expensive as they require the clinician to run the counseling and sound therapy sessions.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is an object of the present invention to provide an interactive gaming system and associated auditory training method to facilitate auditory training for sufferers of tinnitus, or to at least provide the public with a useful choice.

SUMMARY OF THE INVENTION

In a first aspect, the present invention broadly consists in an interactive gaming system for a user suffering tinnitus comprising:
a game machine configured to provide a game scenario in which the user's performance in the game scenario is based on the user's response to audio cue arrangements comprising a combination of sounds, and where at least one of the sounds has one or more sound characteristics that are configured based on one or more sound characteristics of the user's perceived tinnitus;
an audio delivery device or devices that are driven by the game machine to present the audio cue arrangements to the user in accordance with the game scenario; and
a user interface in signal communication with the game machine and which is operable by a user to interact with the game scenario by responding to the audio cue arrangements.

In one form, the game machine is in the form of a personal computer, whether laptop or desktop. In other forms, the game machine may be in the form of suitable programmable electronic device, whether portable or otherwise, including but not limited to a mobile phone, smart phone, PDA, tablet, e-reader device, video game console or the like. The audio delivery device or devices and user interface are in signal communication with the game machine, and may either be integrated with the game machine or separate devices connected to the game machine via hardwiring or wireless communication.

Preferably, the sound characteristics of the tinnitus as perceived by the user may comprise sound attributes and/or spatial attributes. By way of example, the sound attributes may comprise any one or more of the following: frequency, pitch, bandwidth, loudness, temporal properties, type of stimuli, or any other sound attribute. By way of example, the spatial attributes may relate to the spatial location in 3D auditory space of the sound source location of the tinnitus as perceived by the user. In one form, the spatial attributes of the tinnitus may be represented by a sound direction in 3D auditory space that represents the direction from which the user perceives their tinnitus as originating from relative to a user reference point, such as the center of their head.

In one embodiment, the audio delivery devices are in the form of left and right ear-level audio delivery devices that are worn by the user. By way of example, the audio delivery devices may be in the form of headphones, earphones, hearing aids, Cochlear implants, or any other devices that are configured to be worn on, over, or in the left and right ears of the user. In another embodiment, the audio delivery device(s) comprise one or more non-worn speakers.

Preferably, the audio cue arrangement(s) generated by the game machine are provided in the form of left and right audio signals that are converted to audible sound by their respective left and right audio delivery devices. More preferably, the left and right audio signals generate audio cues having desired sound and/or spatial attributes. For example, the audio signals may generate audio cues having virtual sound source locations within a 3D auditory space such that the sounds appear to originate from desired directions within the auditory space.

Preferably, the game scenario has multiple game levels, and each level comprises one or more audio cue arrangements that may be selectively presented to the user for interaction. The audio cue arrangements may be preconfigured, dynamically generated in real-time during gameplay, or a combination of these.

In one form, each audio cue arrangement may comprise a sequential playback of sounds or stimuli in accordance with a playback timeline. The stimuli may be presented continuously in the playback timeline or in a spaced-apart manner according to a variable or constant spacing interval. Additionally or alternatively, the audio cue arrangement(s) may be configured to present two or more stimuli simultaneously or with overlap at one or more points in the playback timeline.

Preferably, the audio cue arrangements may comprise background noise or ambient sounds, either presented constantly or intermittently with the stimuli during the playback timeline.

In one form, each game level of the game scenario may comprise the presentation of a dynamically generated audio cue arrangement or one or more preconfigured audio cue arrangements that are looped (repeated) or sequentially presented.

Preferably, the audio cue arrangement presented to the user is dynamically modified or updated based on the user feedback and in accordance with the game scenario.

The playback of the audio cue arrangements may be initiated by the user operating the user interface and/or in accordance with predetermined gameplay timings.

Preferably, the user interface may be any form of any suitable electronic device enabling the user to provide user feedback. In one form, the user interface may be any form of hand operable device such as, but not limited to, a computer keyboard, computer mouse, game controller, joystick, touch screen, or the like.

In some forms, the interactive game system may comprise a visual display screen that depicts elements or features or other visual information relating to the game scenario. The visual display may be integrated with the game machine or may be a separate component in signal communication with the game machine. By way of example, the visual display screen may be configured to display user performance data relating to the user's gameplay performance, such as a gameplay timer, score, current game level, and/or other training related information, such as training session number and/or training day.

Preferably, the game machine customises the game scenario and/or audio cue arrangements of the game scenario to the user based on a user tinnitus profile that defines one or more measured or assessed tinnitus sound characteristics of the user. In one form, the user tinnitus profile may be in the form of an electronic data file that is received or retrieved by the game machine. In another form, the user tinnitus profile may be generated by the game machine in response to user interaction. By way of example, the game machine may provide interactive measurement testing for assessing one or more sound characteristics of the user's tinnitus.

Preferably, the game machine is configured to run an initial user calibration function prior to commencing gameplay to re-assess the user's perceived tinnitus sound characteristics relative to those stored in the tinnitus profile of the user and generate calibration data. More preferably, the game machine is configured to customise the game scenario based on the user's tinnitus profile data and calibration data.

Preferably, the game machine is configured to store the calibration data and the user's gameplay performance data in one or more electronic data files in an associated data storage medium at the end of a gameplay session. More preferably, the game machine is configured to retrieve previous user calibration data and performance data when configuring the next gameplay session for the user.

The game scenario may be configured to provide any one or more of various forms of audio training for tinnitus rehabilitation, including, but not limited to, sound localization training, frequency discrimination training, frequency categorization training, attention training, tone pips stimulation on broad frequency band, or any combination of these. The following forms of the game scenario are intended to provide non-limiting examples of possible game scenario configurations.

In a first form, the game scenario is configured to provide sound localisation training for the user. In this form, the audio cue arrangements may comprise a combination of one or more distracter sound(s) having sound characteristics that substantially correspond to at least one characteristic of the tinnitus as perceived by the user and one or more target sound(s) having no such correspondence to the user's perceived tinnitus, and the game machine may be configured to advance the user in the game scenario in response to user feedback indicative of the user identifying the target sound(s).

In one embodiment of the first form, the game scenario is a sound localisation game in which the user is required to perform game tasks by tracking and locating the target sounds. By way of example, the sound localisation game may be in the form of a 'terrain game' where the user is required to navigate their player position about a game terrain presented on a visual display to perform the game tasks based on the audio cue arrangement as a guide. The game terrain may be either 2D or 3D. In this embodiment, the game scenario presents the user with an audio cue arrangement comprising a target sound at a target location on the game terrain and one or more distractor sounds located at other locations on the terrain grid, and the user is required to move toward the target location via the user interface to advance in the game scenario. In this embodiment, the feedback indicative of the user identifying the target sound(s) is in the form of the user moving their player position closer to the target locations of the target sounds.

In a second form, the game scenario is configured to provide categorization training (CT) and/or discrimination training (DT) for the user. In this form, the audio cue arrangements may comprise a combination or one or more target sounds and one or more distractor sounds, the sound characteristics of each sound being configured based on one or more sound characteristics of the tinnitus as perceived by the user, and the game machine may be configured to advance the user in the game scenario in response to user feedback indicative of the user correctly categorizing target and distractor sounds or discriminating between the target and distractor sounds. In one form, the game scenario may be configured to provide CT or DT in relation to a particular sound characteristic, such as frequency.

In one embodiment of the second form, the game scenario may be in the form of a 'submarine game' where the user is required to identify and shoot enemy submarines based on the audio cue arrangements as a guide. In this embodiment, the game scenario presents the user with an audio cue arrangement comprising a sequence of one or more target sounds representing enemy submarines and distractor sounds representing friendly submarines and the user is required to identify which sounds represent the enemy submarines for shooting via the user interface to advance in the game scenario.

The game scenario may be configured to run or is switchable between either a CT mode or DT mode, and the sound characteristics of the target and distractor sounds are configured according to each mode of training.

Preferably, the submarine sounds may be generated to originate from different directions in 3D auditory space.

In a second aspect, the present invention broadly consists in a computer readable medium upon which computer readable instructions are stored for configuring a game machine to provide an interactive auditory training game having a game scenario for a user suffering tinnitus in which the user's performance in the game scenario is based on their response via an operable user interface to one or more audio cue arrangements presented to the user over one or more audio delivery devices and in which the audio cue arrangement(s) comprise a combination of sounds, and where at least one of the sounds has one or more sound characteristics that are configured based on one or more sound characteristics of the user's perceived tinnitus.

In a third aspect, the present invention broadly consists in an interactive auditory training game for a user suffering tinnitus, the game being configured to run on a game machine and providing a game scenario in which the user's performance in the game scenario is based on their response via an operable user interface to one or more audio cue arrangements presented to the user over one or more audio delivery devices and in which the audio cue arrangement(s) comprise a combination of sounds, and where at least one of the sounds has one or more sound characteristics that are configured based on one or more sound characteristics of the user's perceived tinnitus.

In a fourth aspect, the present invention broadly consists in a method of interactive auditory training for a user suffering tinnitus, comprising the steps of
  assessing one or more sound characteristics of the tinnitus as perceived by the user and storing the assessed information in a user tinnitus profile;
  configuring an interactive auditory training game having a game scenario in which the user's performance in the game scenario is based on their response to one or more audio cue arrangements comprising a combination of sounds, and where at least one of the sounds has one or more sound characteristics that are configured based on one or more sound characteristics of the user's tinnitus profile; and
  providing the interactive auditory training game to the user to play in accordance with a training plan.

Preferably, the method further comprises the step of re-assessing one or more sound characteristics of the user's tinnitus prior to a gameplay session in the training plan and updating the user tinnitus profile with the re-assessed characteristics for reconfiguring the game scenario to the updated user tinnitus profile. More preferably, the step of re-assessing the one of more sound characteristics of the user's tinnitus occurs prior to each gameplay session.

In a fifth aspect, the present invention broadly consists in an interactive gaming system for a user suffering tinnitus comprising: an electronic game machine configured by stored game data to provide a game scenario in which the user's performance in the game scenario is based on the user's response to generated audio cue arrangements comprising a combination of sounds, and where at least one of the sounds in the audio cue arrangements has one or more sound characteristics that are configured based on stored user tinnitus profile data indicative of one or more sound characteristics of the user's perceived tinnitus; an audio delivery device or devices that are in signal communication with and driven by the game machine via audio signals to present the audio cue arrangements to the user in accordance with the game scenario; and a user interface in signal communication with the game machine and which is operable by a user to interact with the game machine via user feedback signals in response to the presented audio cue arrangements to advance in the game scenario.

The second-fifth aspects of the invention may have any one or more features mentioned above in respect of the first aspect of the invention.

The phrase "ear-level audio delivery device" as used in this specification and claims is intended to cover any type of audio delivery device that can be worn or located on, over or in a person's ear, whether a standalone audio component or integrated with another electronic device or system, and which can be driven to produce audible sound, including, by way of example only and not limited to, headphones, ear buds, hearing aids, and Cochlear implants.

The phrase "3D auditory space" as used in the specification and claims is intended to mean, unless the context suggests otherwise, the volume of space, whether external to a person or internal, from which actual or perceived sounds are determined as originating from according to the sound localisation processing of the person's brain.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

As used herein the term "and/or" means "and" or "or", or both.

As used herein "(s)" following a noun means the plural and/or singular forms of the noun.

The invention consists in the foregoing and also envisages constructions of which the following gives examples only.

BRIEF DESCRIPTION OF THE DRAWINGS

Preferred embodiments of the invention will be described by way of example only and with reference to the drawings, in which:

FIG. 15B shows a graph of the mean change in subjective tinnitus pitch-match of

FIG. 15A with reference to +/−one standard deviation for the Terrain group;

DETAILED DESCRIPTION OF PREFERRED EMBODIMENTS

1. Overview

The present invention relates to an interactive gaming system and associated method of auditory rehabilitation training with the interactive game system for sufferers of tinnitus. The game system and rehabilitation method aims to reduce the user's perceived tinnitus through a process of learning-related plasticity.

Figure 1:
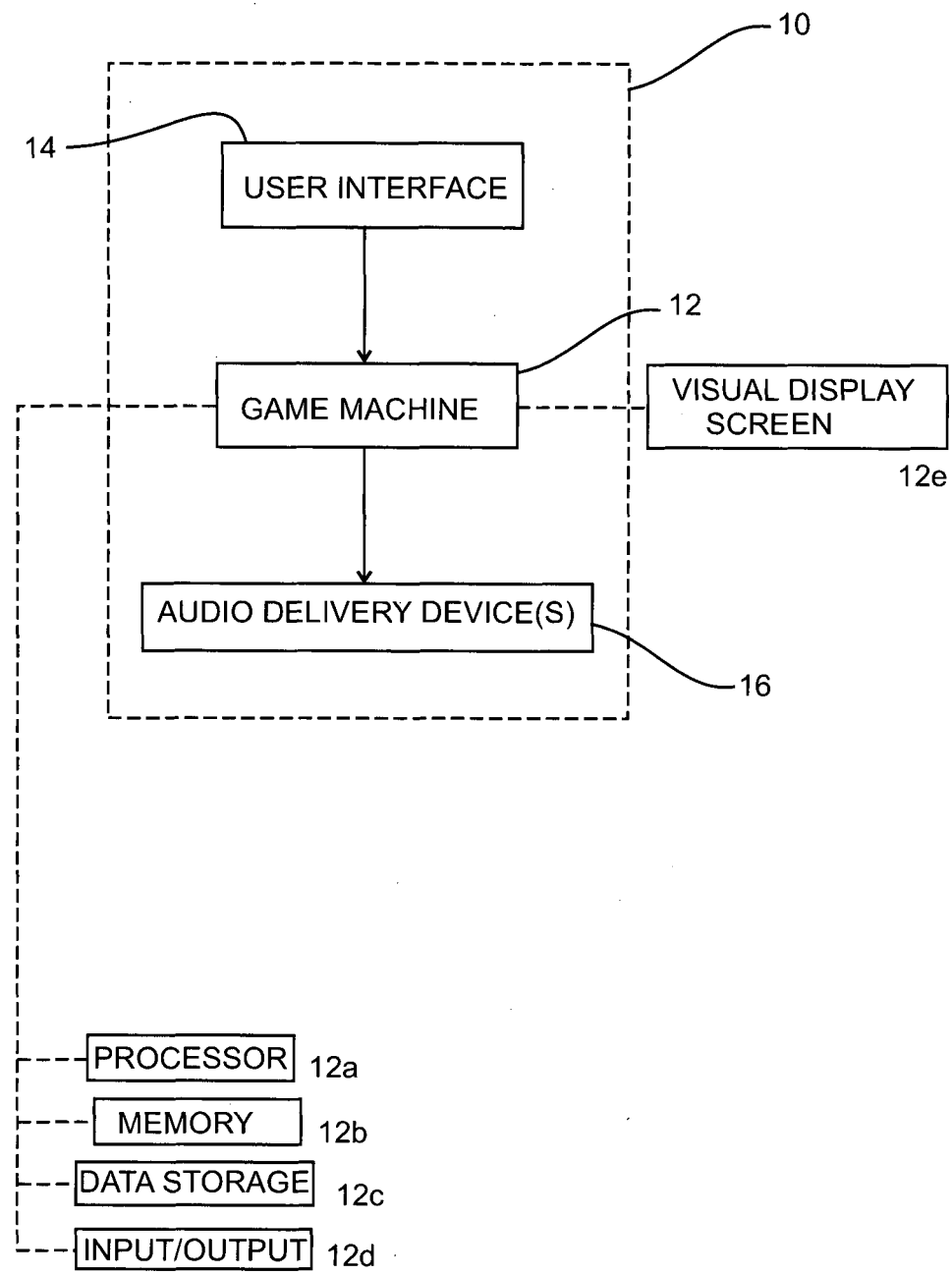
FIG. 1 shows a schematic block diagram of the main components of an interactive gaming system in accordance with an embodiment of the invention.

Referring to FIG. 1, an embodiment of the interactive gaming system 10 comprises a game machine 12, and a user interface 14 and audio delivery devices 16 that are either integrated with or separate components that are in signal communication with the game machine 12. The game machine 12 is configured to provide an interactive game scenario in which the user's performance in the game scenario is based on their response to an arrangement of audio cues. The audio cues comprise a combination of sounds and where at least one of the sounds has one or more sound characteristics that are configured based on one or more sound characteristics of the tinnitus as perceived by the user. The sounds may comprise target sounds and distractor sounds as discussed further below, and ambient or background sounds may also be provided in some forms of the game scenarios. The game scenario and audio cue arrangements may be stored as computer-readable game data in memory or an accessible data storage medium as will be appreciated. The game scenario may be in the form of a series of computer-readable instructions stored in the game data.

Each game scenario is configured with objectives or game tasks, and is provided with a performance or progression indicator in the form of the user completing a series of levels in the game scenario, a scoring system, or a combination of level progression and scoring, or any other performance measure. In one form, the game scenarios may be configured to provide sound localisation training. In another form, the game scenarios may be configured to provide categorisation training (CT) and/or discrimination training (DT).

Typically, each game scenario allows the user to complete the game objectives or tasks by rewarding user interaction or feedback that is indicative of the user identifying and attending to the target sounds in the audio cue arrangement(s) by for example progressing the user to the next level and/or increasing their game score. Optionally, each game scenario may also punish or penalise users for attending to distracter sounds by halting their progress through the game scenario and/or reducing their game score for example. Ultimately, each game scenario has the objective of rewarding the user for attending or focusing on the target sounds while ignoring the distracter sounds.

System Hardware

The electronic game machine 12 may be any form of hardware device or system that is capable of running or playing the auditory attention training game, which may be in the form of software or an application program. By way of example, the game machine may be a personal computer, whether desktop or laptop, Personal Digital Assistant (PDA), mobile phone, smart phone, tablet (e.g. iPad), portable audio player, video game console or any other suitable electronic hardware device or system. The game machine typically comprises a processor 12a for executing computer-readable or software instructions, memory 12b, data storage medium 12c such as a hard disk or flash drive or similar for storing data, and an input/output interface 12d for user input/output devices and for interaction with external devices. It will be appreciated that the game machine may be any form of hardware device or system that is configurable to run a game scenario in the form of an application program or software and which has a sound processor for generating and/or delivering sounds in the form of audio signals. Optionally, the game machine may comprise a visual display screen 12e. The display screen may be integrated with the game machine or connected to the game machine for displaying any graphical aspects of the game scenario for additional user interaction in combination with the audio cue arrangements. Optionally, the game machine may also provide tactile feedback devices, which may be separate or integrated with the user interface, such that the game machine can deliver tactile feedback (e.g. vibrations or the like) to the user during game interaction.

The user interface 14 is connected to or otherwise in signal communication with the game machine 12 either via hardwiring or wireless communication. The user interface may be any form of device that is operable by a user to interact with the game machine. By way of example, the user interface may include any one or more of the following: keyboard, mouse, joystick, control pad, game controller, touch screen, or any other operable device that is configured to generate user feedback signals for processing by the game machine. The user interface may operate in cooperation with the visual display screen of the game machine, if provided, or alternatively as a standalone user interface without any associated visual information on a visual display screen.

The audio delivery device or devices 16 of the game system are connected to or in signal communication with the game machine via hardwiring or wireless communication. The audio delivery devices may be in the form of speakers or ear-level left and right audio delivery devices that are intended to be worn or located on, over or in a person's ears, such as but not limited to headphones, earbuds, hearing aids, cochlear implants, or any other such audio delivery devices. In this embodiment, audio delivery devices are in the form of left and right ear-level audio delivery devices worn on, over or in the left and right ears of the user during the interactive gameplay. The sound processor of the game machine is configured to generate the left and right audio signals to generate spatial sounds that are presented or delivered to the user so as to be perceived to originate or emanate from a predetermined direction and/or location in 3D auditory space, whether within the user's head or external head using virtual acoustic technology, such as Virtual Acoustic Space (VAS) techniques or virtual surround sound processing. It will be appreciated that spatial audio signals with virtual sound source locations are not essential in all embodiments, and monaural or binaural signals may be generated such that audio sounds or cues originate at either the left ear or right ear, or appear to originate in the centre of the user's head if desired in alternative embodiments. For embodiments in which the audio delivery devices comprise one or more speakers, the speakers may be in the form of left and right speaker pairs, surround sound speakers, or any other single of multi-speaker speaker configuration. It will be appreciated that the audio delivery devices may additionally comprise integrated or associated sound processors and/or amplifiers for receiving and processing of the audio signals from the game machine prior to driving the audio transducers of the audio delivery devices to generate the audio sounds. The speakers may be any form of speaker units that are capable of delivering/presenting audible sound to a user displaced from the speaker units including, but not limited to, stand-alone speaker units driven directly by the game machine or via an audio amplifier or controller, speaker modules integrated within or connected to other electronic devices such as computers, or any other type of non-worn speaker.

System Customisation and Configuration

Figure 2:
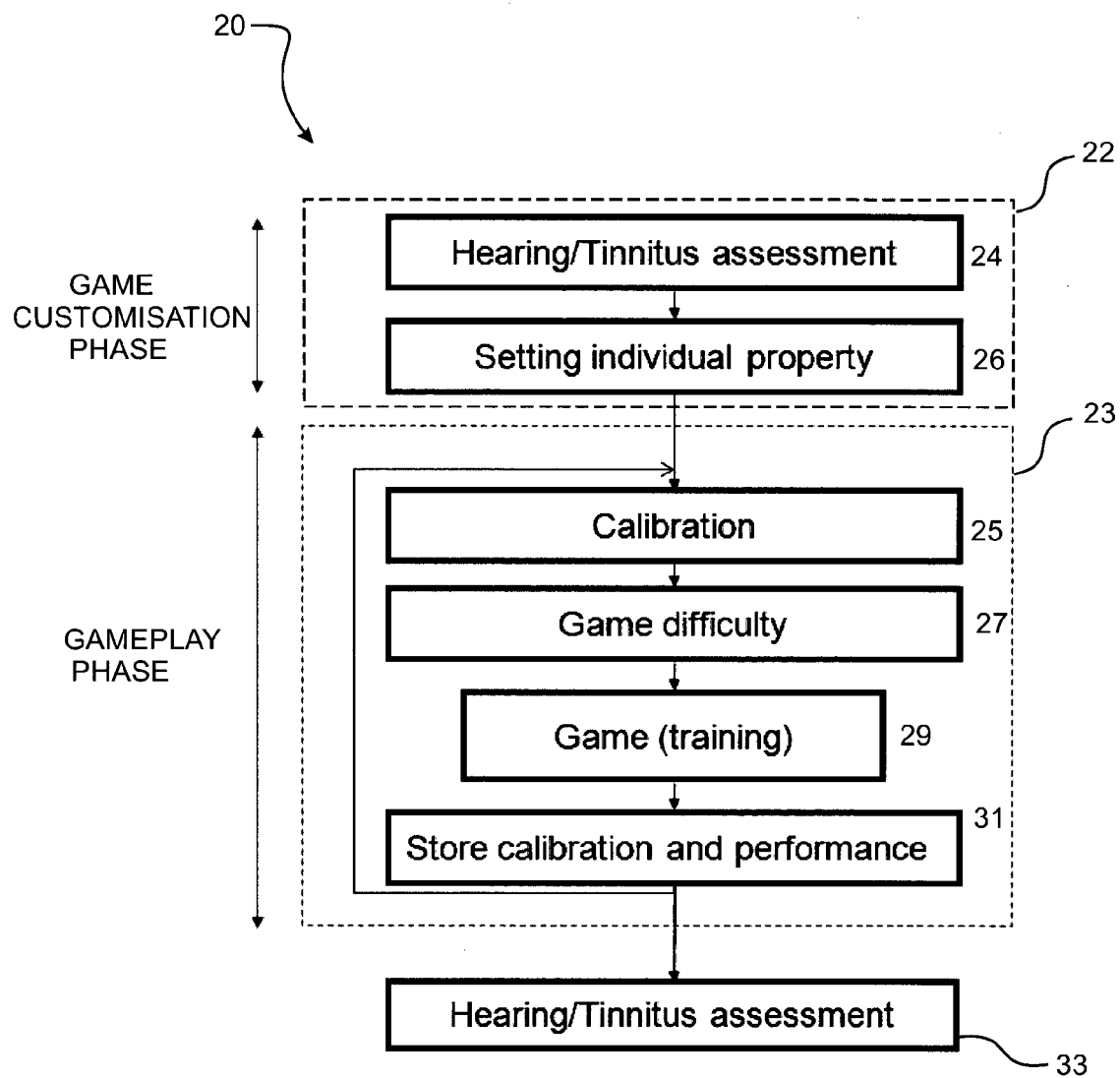
FIG. 2 shows a flow diagram of the main steps in a method of providing an interactive auditory rehabilitation game for sufferers of tinnitus using the interactive game system of FIG. 1, including a game customization phase and gameplay phase, in accordance with an embodiment of the invention.

Referring to FIG. 2, an overview of an embodiment of the rehabilitation method 20 employing the interactive gaming system is shown. The process starts with an initial game customisation phase 22 which involves diagnosing the user's tinnitus characteristics at assessment step 24. The assessment step 24 may comprise a sound volume calibration diagnosis to determine the user's individual absolute hearing thresholds (audiogram) and uncomfortable loudness levels. Secondly, the user's tinnitus characteristics in the form of sound attributes and spatial attributes are assessed. The tinnitus sound attributes assessed for the user may comprise any one or more of the following: perceived sound characteristics (e.g. sound type, such as but not limited to pure tone, noise, environmental sounds, or any other sounds), bandwidth, temporal properties, loudness (intensity), and pitch. The spatial attributes relate to the location in 3D auditory space of the sound source location of the tinnitus as perceived by the user, i.e. the direction in 3D auditory space from which the user perceives their tinnitus as originating. For example, the user may perceive the tinnitus sound as originating from one ear, both ears, or a location within their head or external to their head. These sound characteristics of the user's tinnitus may be assessed by an audiologist or clinician using various audio tests known to those skilled in the art. The information or data determined from the assessment step 24 is stored in a tinnitus profile for the individual user. In this embodiment, the tinnitus profile is stored electronically as a digital data file in a data storage medium (portable or otherwise) for use by the interactive game system, but alternatively the assessment information may be manually recorded on other mediums and input into the interactive game system manually in alternative embodiments.

The next step in the game customisation phase 22 is the setup step 26 for configuring and customising the game scenario for the individual user. The setup step 26 receives the tinnitus profile data and involves setting the various game scenario parameters in view of that data either manually or automatically as will be explained further with reference to FIG. 3.

Figure 3:
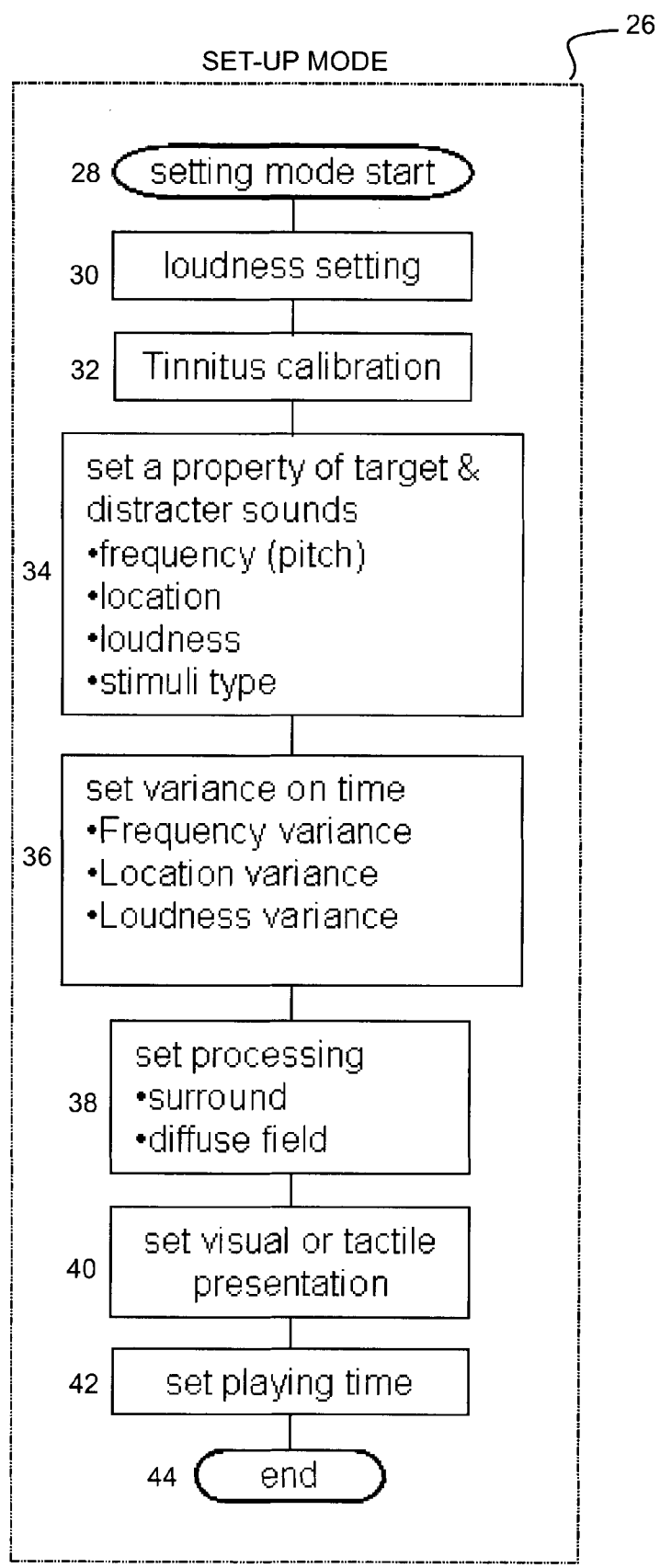
FIG. 3 shows a flow diagram of the main steps in a set-up configuration process of the game customization phase of the method of FIG. 2 in accordance with an embodiment of the invention.

Referring to FIG. 3, the setup step 26 commences after start-up 28 with a loudness setting 30. In this embodiment, the user or clinician adjusts the sound level of the game that the user will hear through the audio delivery devices, such as headphones, using behavioural calibration at each frequency band. Then the game audio sounds are equalised to aid the hearing by the user. For example, any frequency that would not beat the user's hearing loss is amplified or alternatively is not used. If the audio delivery devices are hearing aids or cochlear implants, the loudness setting is configured to adjust the overall volume level to a comfortable level for the user. This loudness setting 30 is to ensure that all users, whether they have hearing loss or not, will be able to hear all parts of the game scenario properly and comfortably to get maximum possible benefit of the auditory attention training.

After the loudness setting 30, the tinnitus calibration step 32 is initiated. The tinnitus calibration step 32 may either receive the user's tinnitus profile as previously recorded during the assessment step 24 or alternatively may comprise assessing the user's tinnitus sound attributes above and inputting that data into the setup for the game scenario. For example, if a tinnitus profile is not available for the user, optionally the game machine may be configured to generate the user tinnitus profile in response to user interaction. By way of example, the game machine may provide interactive measurement testing for assessing one or more sound characteristics of the user's tinnitus, similar to the assessments made during the assessment step 24.

The setup then moves to an audio cue configuration step 34 in which the properties of the target sounds and distracter sounds may be customised based on the user's tinnitus profile. Additionally, ambient sounds and background noises in the game scenario may be customised based on the user's tinnitus profile or otherwise. By way of example, the frequency, location, loudness and stimuli type of the target and distracter sounds may be customised based on the user's tinnitus profile as explained further below, depending on the game scenario and type of training being provided.

In regard to frequency, the frequencies of the target and distracter sounds may be controlled to be categorised as a sound group around the tinnitus pitch that is to be decreased in sensitivity and reduced cortical representation or alternatively to be discriminated at the pitch which is wanted to be reinforced in sensitivity and changes in cortical representations. The frequency (pitch), bandwidth and the Just Noticeable Differences (JNDs) for the target and distracter sounds are customised based on the user's tinnitus pitch, loudness and user's audiogram based on the user's tinnitus profile. A number of frequencies and frequency groups may be defined to attract or distract attention.

In regard to the location of the target and distracter sounds, the locations of the sounds or perceived sound origins or sources are located at virtual 3D spaces in 3D auditory space using Head Related Transfer Function (HRTF) such as via virtual acoustic processing technology and sound localisation techniques known to those skilled in the art. Various techniques for altering the perceived location of sound in 3D auditory space are known, including using one or more of the following, in combination and/or alone, Interaural Time Difference (ITD), Interaural Level Differences (ILD), and Head-Related Transfer Functions (HRTFs). ITD and ILD tend to be used to vary the perceived lateral location of the sound along the midline axis between a person's ears (e.g. at center of a head or left or right), but HRTFs enable sound to be localised outside of the head and at a desired direction having an azimuth and elevation relative to a reference point, such as the center of the user's head. The locations of distracter sounds may be controlled to be at "bad" locations such as the user's perceived tinnitus location. The objective is to decrease sensitivity and reduce cortical representation at the bad location. The target sounds are at "good" locations, e.g. not overlapping with the tinnitus location, and the objective is to reinforce sensitivity and enhance graphical representations of sounds in such locations. The location of the target and distracter sounds are controlled to either attract or distract attention as desired.

In regard to loudness, the loudness of the target and distracter sounds are customized and controlled to be suitable for the user's hearing level at each frequency. Additionally, the loudness of the sounds is controlled to attract or distract attention accordingly.

In regard to stimuli type for the sounds, these may be configured to either have or not have a context or intrinsic behaviorally relevant meaning and are used to attract or distract attention accordingly. The stimuli may be customized to work to aid in the development of a process of learning-related plasticity which occurs through involvement of top-down and bottom-up processes, including attention and discrimination/categorization training. Examples of possible stimuli types for the target and distracter sounds include any one or more of the following: tone, broadband noise, narrow band noise, low frequency noises, natural sounds, speech, animal sounds, music, mechanical sounds, or the like. The temporal characteristics of the target and distracter sounds, for example steady and continuous or pulsed may be customized. Optionally, the stimuli may or may not be presented in combination with supplementary visual information or tactile information in the game scenario to either attract or distract attention relative to "bad" audio distractor sounds, such as the tinnitus, and with decreased sensitivity and cortical representations as desired or with "good" audio target sounds in which it is desired to reinforce sensitivity and cortical plasticity.

The next step in the setup 26 is configuring variance parameters 36 relating to the arrangement of audio cues presented during the game. The variance parameters may be configured to reinforce or punish attention to target or distracter sounds, to control the difficulty of the game scenario, or to make a progressive desensitization of the target sound over a time sequence for example. The variance parameters include loudness variance, frequency variance and spatial location variance. For example, for loudness variance the amplitude modulation may be customized pseudo-randomly or regularly to alter attention to the target and/or distracter sounds, or alternatively an incremental and desensitization technique may be used to alter attention to the sounds.

The setup configuration then moves to the sound field parameters configuration 38. In the sound field configuration, parameters relating to the use of virtual surround sound processing to create target and distracter sounds at desired locations in 3D auditory space may be configured. By way of example, this may include configuring HRTFs for the user or otherwise customizing the virtual surround sound processor to accommodate the type of audio delivery devices being employed by the interactive game system. Diffuse-field equalizing of the game sounds may also be employed and customized for the user's audio delivery devices, for example headphones or hearing aids or other ear-level audio delivery devices.

If the interactive game system is provided with a visual display and/or tactile feedback devices, such as vibration devices or similar, the setup would include parameters for configuring such visual or tactile presentation to assist the audio attention training to reinforce or punish audio cues or to focus or divide or distract attention to contribute to game difficulty.

The setup then moves to the playtime configuration 42 in which the playing time and other timings of the game scenario may be customized, and once this is done the setup configuration ends 44.

Reverting to FIG. 2, at the completion of the game setup 26 of the game customization phase 22, the rehabilitation method moves to gameplay phase 23. Upon initiation of the gameplay phase 23, the interactive game receives or retrieves the setup data generated during the game customization phase and configures the game scenario for the auditory training according to the desired treatment or training plan over the desired number of training days. As shown on FIG. 2, the gameplay phase 23 starts with an initial calibration 25 and game difficulty 27 configuration steps before moving to the interactive game training 29. At the end of gameplay, the interactive game system stores the initial calibration data and the user's training and performance data in the form of electronic data files in memory or an associated accessible data storage medium. The gameplay phase 23 of the rehabilitation method will now be described in more detail with reference to FIGS. 4 and 5A-5I.

Figure 4:
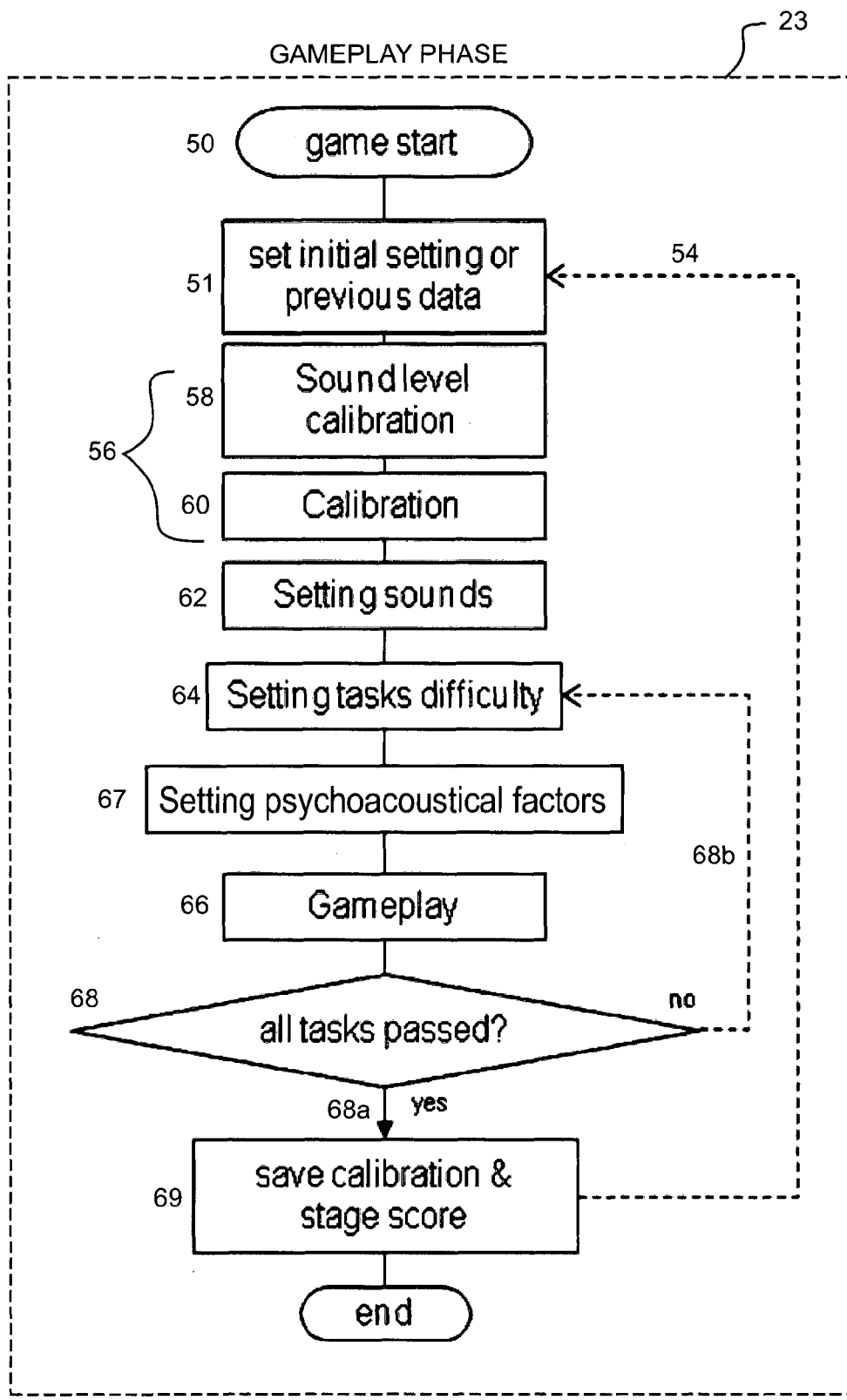
FIG. 4 shows a flow diagram of the main steps in the gameplay phase of the method of FIG. 2 in accordance with an embodiment of the invention.

Referring to FIG. 4, upon starting 50 of the gameplay phase 23, the setup data from the game customization phase 22 is received or retrieved from memory by the interactive game system for configuring and customizing the game scenario to the user and their perceived tinnitus properties at the initial setup 52. Additionally, if the game scenario is being restarted after a previous training session, the calibration and performance data may be retrieved from memory to refine the setup data for the next training session with the game scenario as shown at 54. Each new gameplay session, whether the first in a training session or a subsequent session, begins with an initial gameplay calibration phase 56. In this embodiment, the gameplay calibration phase 56 comprises a sound level calibration 58 and a tinnitus assessment 60.

Figure 5A:
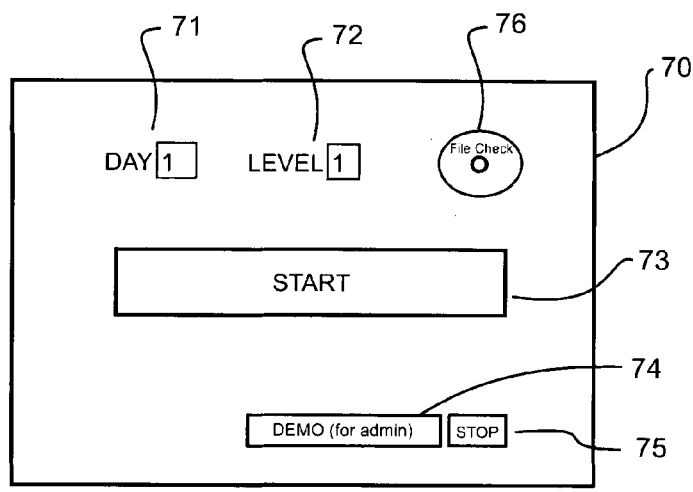
FIGS. 5A-5I show screenshots of graphical user interface (GUI) screens of an initial calibration mode of the interactive game system in accordance with an embodiment of the invention.

Referring to FIG. 5A, the initial game start screen is displayed on the visual display of the interactive game system during initial setup. As shown, the startup screen or GUI 70 in this embodiment displays the training day 71 and game scenario level 72 along with providing a start button 73 for initializing gameplay. In this embodiment, a demo of the game scenario may be initiated with button 74. A stop button 75 is also provided for halting the program. A file check indicator 76 may be provided to indicate whether the setup and any previous calibration and performance data files are available for the initial game scenario customisation.

Figure 5B:
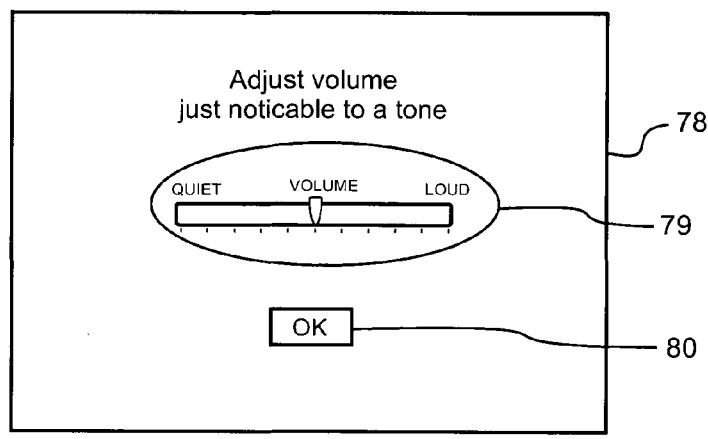

Once the start button 73 is initiated, the gameplay phase moves to the sound level calibration 58 of the gameplay calibration phase 56. Referring to FIG. 5B, the sound level calibration GUI 78 is shown. This sound level calibration is used to configure the sound amplification in the game machine to the user's audiogram. This calibration extracts the user's absolute hearing threshold at 1 kHz so that the user's audiogram can be applied at the threshold point. In this calibration GUI, a 1 kHz pure tone is presented or delivered to the user over the audio delivery devices and the user must adjust the volume slider scale to a level where the tone is just noticeable. Once the volume level has been adjusted, the user moves to the next step in the calibration phase by pressing the "Ok" button 80.

Figure 5C:
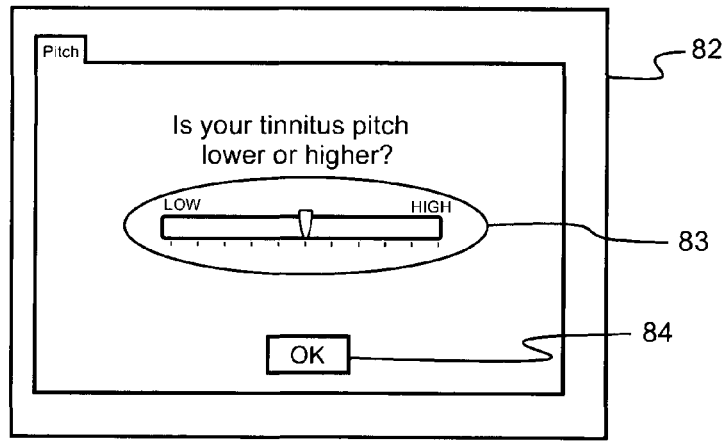
Figure 5D:
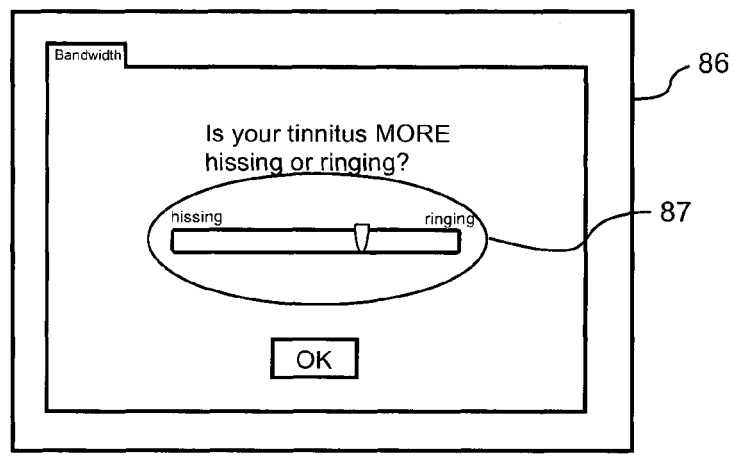

The next step in the gameplay calibration phase 56 is the tinnitus assessment 60 that involves a measurement of pitch, bandwidth, loudness, and 3D location of the user's tinnitus. The tinnitus assessment 60 utilizes the user's tinnitus profile as provided in the initial setup data to arrange the assessment such that the calibration is a refinement or modification of the user's tinnitus profile in case anything had changed during the training sessions or since the user's initial tinnitus assessment in the game customization phase 22. Referring to FIG. 5C, a screenshot of the display screen with the tinnitus pitch calibration GUI 82 is shown. The function associated with this GUI generates a sound over the audio delivery devices at the user's tinnitus pitch as determined in the initial setup data. The user can then self-check this tinnitus pitch for accuracy and adjust the pitch either lower or higher using the adjustable pitch scale 83 and can then move on to the next calibration step by activating the "ok" button 84. FIG. 5D shows a screenshot of the bandwidth calibration GUI 86 in which the user may conduct a self-check of the tinnitus bandwidth. The function associated with the bandwidth calibration GUI is configured to generate a sound over the audio delivery devices at a bandwidth corresponding to the initial setup data of the user's tinnitus profile. The user may then adjust the real-time bandwidth of the sound using the adjustable bandwidth scale 87 to more closely match to their perceived tinnitus bandwidth if required. For example, the scale may range between a hissing sound and a ringing sound.

Figure 5E:
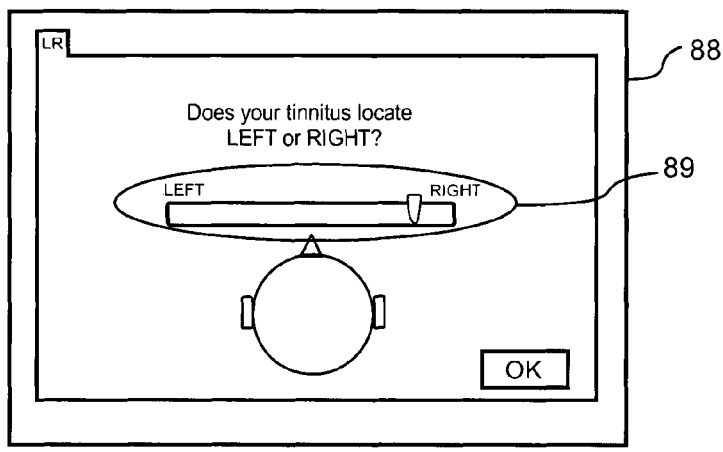
Figure 5F:
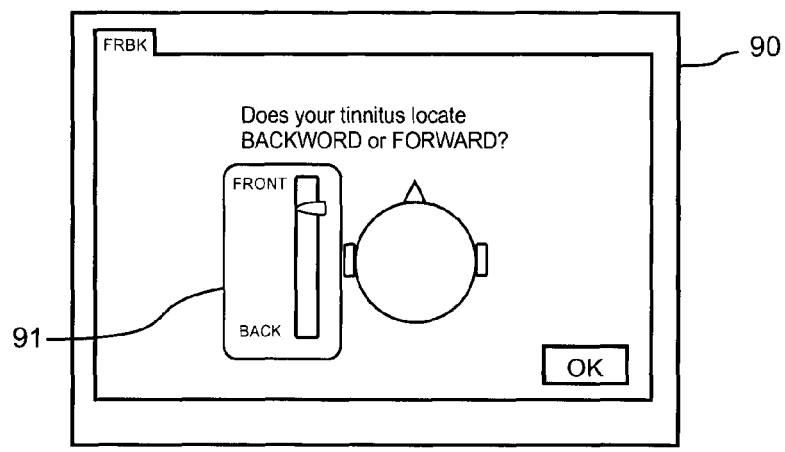
Figure 5G:
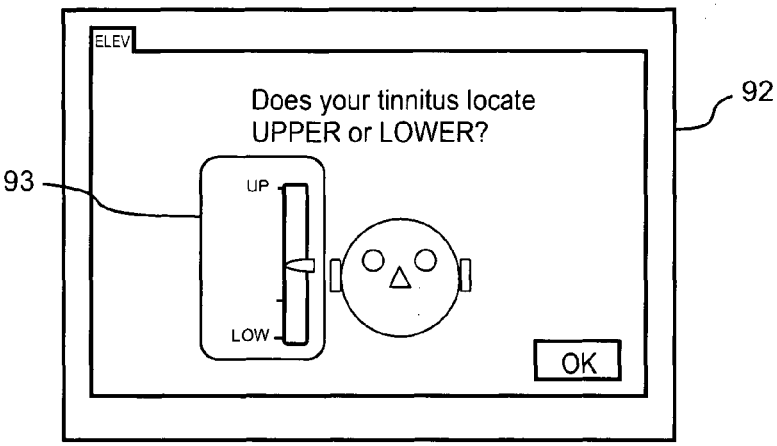

The tinnitus assessment 60 then measures the 3D location (spatial attributes) of the origin of the tinnitus as perceived by the user. The test sound used for assessing the spatial attributes may be a test sound having sound attributes that substantially correspond or match those of the user's tinnitus as previously assessed, for example pitch and bandwidth. With reference to FIGS. 5E-5G, screenshots of 3D location calibration GUIs are shown in which the user can adjust the azimuth (left or right and backward or forward) and elevation (up or down) the perceived 3D location of the tinnitus relative to the center of their head. In this embodiment, the spatial attributes of the user's perceived tinnitus are represented as a directional vector to the perceived tinnitus sound source location, and is represented by an azimuth angle (between 0-360° relative to a horizontal plane at the center of the head, and an elevation angle (between −90° to 90°) relative to the center of the head. However, it will be appreciated that the spatial attributes of the perceived tinnitus location may be represented in any other form, including Cartesian coordinates relative to the 3D auditory space.

In this embodiment, the user firstly calibrates the azimuth with the left or right adjustment 89 in GUI 88 and then whether the tinnitus is located toward the front or back of the head with adjustment scale 91 of GUI 90. Once the azimuth of the user's tinnitus 3D location is adjusted, the user is then presented with a GUI 92 for adjusting via scale 93 to measure the elevation of the user's perceived tinnitus location toward the upper or lower portion of the head. In each of the 3D location calibration GUIs, 88,90,92 the associated functions are configured to generate the 2D test sound at their respective location determined previously by the user's tinnitus profile as provided in the setup data. Therefore, the adjustments made by the user in GUIs 88,90,92 are refinements of that 3D location (azimuth and elevation) relative to the changes that may have occurred since last playing the training game or since the initial tinnitus assessment was made during the game customization phase of the rehabilitation method.

Figure 5H:
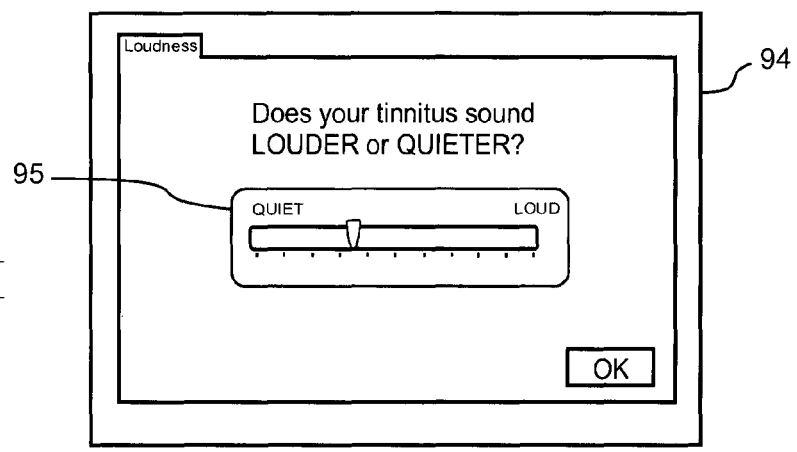
Figure 5I:
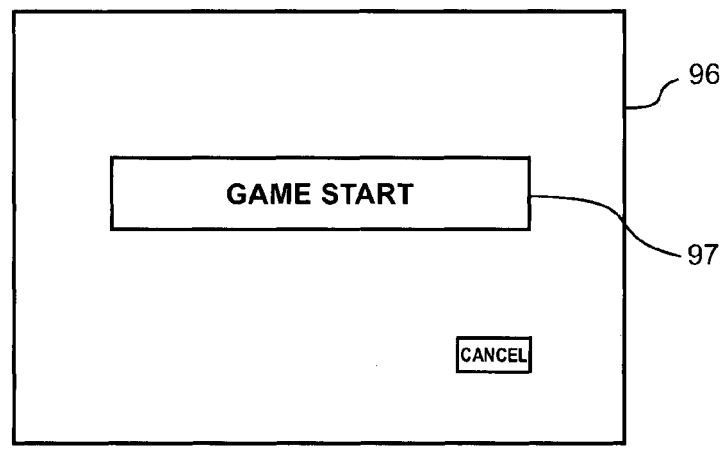

Referring to FIG. 5H, the tinnitus assessment then moves to a loudness calibration GUI 94. The loudness calibration GUI has an associated function that presents the user with a test sound originating from the 3D location determined during the 3D calibration process such that the test sound is 3D in that it has one or more characteristics corresponding to the sound attributes of the user's perceived tinnitus and is also at the 3D location from which the user perceives their tinnitus as originating. The user can adjust the loudness level using scale 95 to match the loudness of their tinnitus. Once the gameplay calibration phase 56 is completed, the user is presented with a game start GUI 96 having a game start button 97 for initiating the gameplay as shown in FIG. 5I. Prior to gameplay initiation, the calibration data measured during the gameplay calibration phase 56 reconfigures the game scenario parameters if necessary relative to the parameters set based on the initial setup data at 52. For example, at 62 the audio parameters of the target and distracter sounds may be configured based on any new calibration data measured, including variances in the frequency, pitch, location, and loudness of the target and distracter sounds employed in the game scenario. Additionally, the difficulty of the training delivered by the game scenario is configured based on the user's previous performance (if any) or the stage in the training program, and this may occur automatically based on the user's previous performance data, for example current game level or game score or training day in accordance with the game scenario tasks or levels. For example, at 64 the game scenario difficulty is configured automatically. The difficulty may be increased by any one or more of the following parameters, depending on the type of game scenario and training being provided:

Decreasing noticeable differences of frequency and location between target and distracter sounds.
Decreasing loudness and/or modulation of target sounds.
Increasing number of target sounds.
Increasing number of distracter sounds.

Increasing or use of unfamiliar types of stimuli.

Increased occurrence of audio cues or speed or timing of presentation of audio cues.

Decreasing any supplementary visual or tactile information in the game scenario.

Gameplay

Upon initiating the game start button 97, the user begins the game scenario 66 that is shown on FIG. 4 based on the configured settings. As previously described, the game scenario provides the user with a task or tasks or end objectives to achieve. The tasks are achieved based on the user's response to the presentation of an arrangement of audio cues over the audio delivery devices. The type of audio cue arrangements and the desired user response required to achieve the game tasks and progress in the game scenario may vary depending on the type of game scenario. For example, in some embodiments of the game scenarios, the user attending to "good" sounds such as target sounds is rewarded and positively reinforced with game progression, while attending to "bad" sounds, such as distracter sounds is punished or results in non-advancement in the game scenario. The objective of this game format is to encourage the user to ignore their tinnitus over time in favor of attending to target sounds to achieve desired objectives. Such auditory attention training over time has the objective of retraining the user to ignore their tinnitus.

Various arrangements of audio cues or sounds may be provided. For example, one or more target sounds and one or more distracter sounds may be presented or delivered to the user over the audio delivery devices according to pre-configured timing sequences, random timing sequences, in an overlapping manner or sequentially, and the location of the target and distracter sounds may be varied in the user's 3D auditory space. In some embodiments of the game scenario, the audio cue arrangements may comprise distracter sounds that have one or more sound attributes corresponding to the user's perceived tinnitus characteristics, whether pitch, frequency, loudness, location or otherwise, whereas the target sounds may have no such corresponding relationship to the user's perceived tinnitus characteristics.

In some embodiments, at step 67 in FIG. 4, the difficulty of the game scenario may be controlled by psychoacoustic measures that determine the progress to the next game stage or level. For a user to progress to a new stage (more difficulty) or the next level of the game, specific training tasks need to be achieved which includes correct scores on frequency, loudness, location or auditory and/or visual reaction time or minimum masking level or any index which is assessed by psychoacoustical methods (e.g. minimum masking level) or attention assessments relative to the stimuli and its condition. At step 68, the game scenario is halted when the specific training tasks are all passed 68a, or the game is reset 68b. For the game scenario tasks completed for a particular level or stage, the calibration data from the gameplay calibration phase 56 and performance data, for example stage, score and/or level is saved into the user's gameplay data file in memory and may be retrieved at 54 when the gameplay is reinitialized.

Some examples of possible gameplay scenarios in some embodiments of the interactive gaming system and the rehabilitation method will now be described in further detail by way of example only. It will be appreciated that other game scenarios may be provided in alternative embodiments.

2. Example 1—Sound Localisation Game Scenario—Terrain Game

With reference to FIGS. 6-10, an example of one type of game scenario configured to provide sound localisation training will be described. In this game scenario, the audio cue arrangements comprise a combination of one or more distractor sound having sound characteristics that substantially correspond to at least one of characteristic of the user's perceived tinnitus and one or more target sounds having no such correspondence to the user's perceived tinnitus, and the game machine may be configured to advance the user in the game scenario in response to user feedback indicative of the user identifying the target sounds.

In this example, the game scenario is called the terrain game and it runs on an interactive gaming system as previously described comprising a game machine that is in single communication with a user interface and audio delivery device to facilitate user interaction with the game machine. As previously described, the auditory training includes a game customization phase and a gameplay phase. The game customization phase generates the game scenario setup files that are used by the game machine to automatically configure the game scenario for the individual user based on their tinnitus characteristic. The game scenario is configured by the game machine based on the setup file for initiation of the gameplay phase. Initiation of the game scenario also has a gameplay calibration phase before the game scenario starts. As previously described, in this embodiment the gameplay calibration phase includes a measurement of pitch, bandwidth, 3D location and the loudness of the user's tinnitus to refine the tinnitus characteristics provided in the user's tinnitus profile in the setup data files should there be any changes. The calibrated tinnitus profile is used in configuring the game scenario if any changes are apparent relative to the initial setup file.

In general, the rehabilitation method may be designed in accordance with a particular training program over a training period. By way of example only, the user may be asked to engage in gameplay for 30 minutes each day for 10 days, although this may be varied as desired. The game scenario difficulty will automatically increase once the user gets a high score or reaches some other performance targets. When the game scenario is completed or a high score or level or some other game milestone is achieved, the game machine will save the user's performance data, such as but not limited to, score, level, response time, errors and gameplay calibration data into one or more data files stored in memory. These performance and calibration data may be used to automatically configure the game scenario for the next training session by the user. Once the training period is complete, all saved performance data and calibration data is stored in memory or output such that it is accessible to an audiologist or clinician to study tinnitus characteristic changes.

Figure 6:
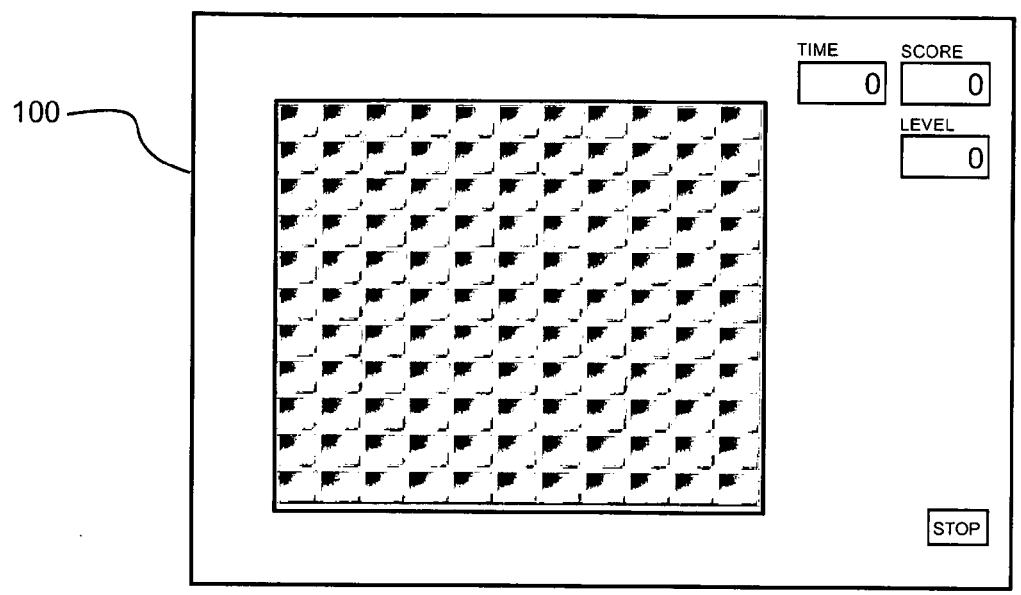
FIG. 6 shows screenshot of game display GUI of the interactive game system when running a terrain game scenario in accordance with an embodiment of the invention.

In the terrain game, the user may be presented with a gameplay screen 100 as depicted in FIG. 6. As shown, the time, score, and level may be displayed along with a stop button to halt the game. Otherwise, the screen is essentially dark with the time, score, level and stop button being visible in FIG. 6. A blank square terrain grid is visible for explanation purposes only, although this is not essential. The gameplay screen 100 may be provided on a visual display integrated with or in signal communication with the game machine as previously described, although it is not essential to the interactive game system.

Figure 7:
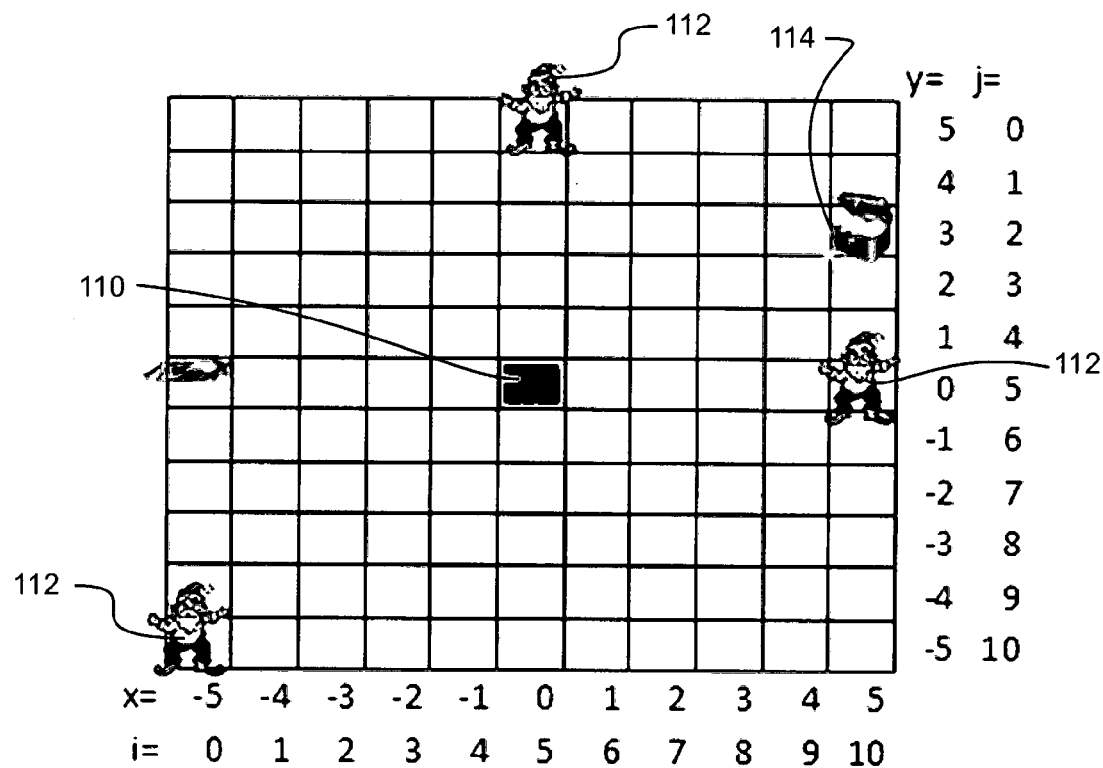
FIG. 7 shows a representation of an arrangement of audio cues on the game terrain grid of the 'terrain' game scenario in accordance with an embodiment of the invention.
Figure 8:
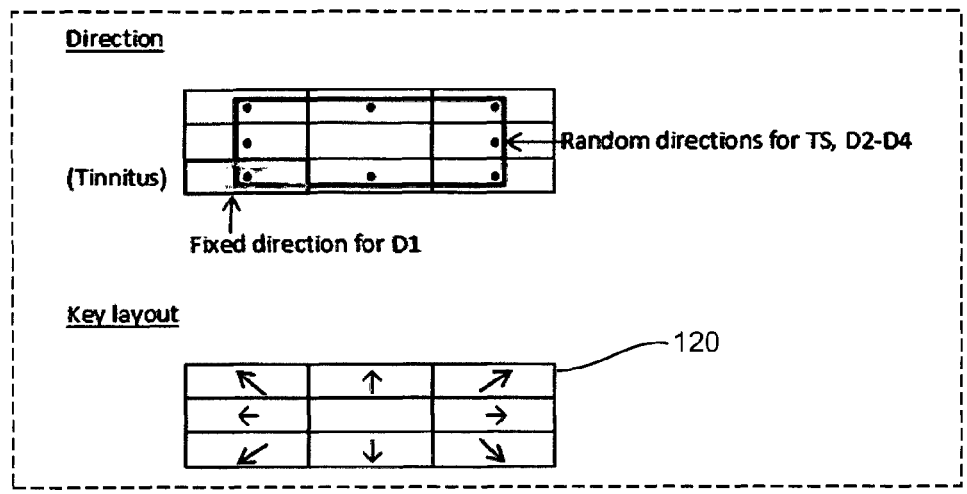
FIG. 8 shows a representation of a user interface for navigating the terrain game scenario in accordance with an embodiment of the invention.

The terrain game requires the user to imagine they are located on a horizontal or planar terrain which may be in the form of a grid providing an array of rows and columns over which the user may traverse as shown in FIG. 7, although none of this is visible to the user during gameplay. The user must rely on the audio cues to navigate the terrain. The user begins with their player position 110 at a predetermined start position, such as in the center of the grid as shown in FIG. 7. The user can then navigate through the grid using user interface, which may be for example a keyboard having 8-keys thereby allowing the user to move forward, backward, left, right, and diagonally in four directions as shown by the key layout 120 in FIG. 8. However, it will be appreciated that any other user interface could be used to enable the user to navigate the terrain grid as required.

The objective of the terrain game is to score points and progress to the next level by collecting "hidden treasures" 114 located on the grid by moving their player location to the hidden treasure location on the grid. Once the user arrives at the hidden treasure on the grid, the screen will flush and collect the treasure and add points to the user's score. The user is required to navigate to the hidden treasures based on an arrangement of audio cues presented to them over their audio delivery devices, such as headphones. As previously described, the arrangement of audio cues includes a combination of target sounds and distracter sounds.

In this terrain game scenario, the target sounds represent treasures and do not correspond to the sound attributes of the user's tinnitus, for example the target sounds (TS) are not stimuli generated at the user's perceived tinnitus pitch ($f_T$), i.e. TS≠$f_T$. The distracter sounds represent "bad elves" 112 and they are sounds corresponding to one or more sound characteristics of the user's tinnitus, for example a sound provided at the user's tinnitus pitch $f_T$ and may also possibly be provided at the user's perceived tinnitus location as superimposed onto the horizontal plane of the terrain grid.

Each of the target and distracter sounds has a variable loudness and originating direction that depends on the user's position on the grid. For the target sounds, the loudness of the sound increases as the user moves or navigates closer toward the treasure and decreases as they move away. Additionally, the perceived direction from which the target sound originates alters or is updated according to the user's position relative to the location of the target sound on the grid as they move.

The distracter sounds may also be 'variable' in that they have a loudness and direction of origin that varies according to the user's navigation around the terrain grid.

Additionally, distracter sounds may be configured to have a fixed loudness and/or sound directions relative to the user regardless of the user position or movement on the grid. Such 'fixed' distracter sounds may be located at the user's perceived tinnitus location such that there is always at least one distracter sound corresponding to the user's tinnitus location.

In this game scenario, the terrain grid is a horizontal 2D plane and the spatial locations of the sounds are restricted to directions relative to the center of the user's head based on an azimuthal direction between 0-360°, with elevation fixed at 0°. From the user's perspective, the azimuthal originating directions may be any desired angle depending on the quality and resolution capability of the sound processor of the game machine and audio delivery devices. However, in other embodiments, the target and distracter sounds may be approximated to the nearest of a discrete set of azimuthal directions relative to the user. For example, in this embodiment there are eight directions at 0, 45, 90, 135, 180, 225, 270 and 315 degrees, so the user may expect a distracter or target sound to originate from any of these directions relative to a horizontal terrain grid at the center of their head and these directions also correspond to the eight directional movements available to the user on the grid via keypad 120. In this example, the terrain game has been described with reference to navigation of a 2D terrain grid using 2D audio cues (i.e. sound origins having configurable azimuthal directions between 0-360° but fixed elevation at 0°). It will be appreciated that in alternative embodiments 3D terrains or landscapes may be provided for the user to navigate through and corresponding 3D audio cues may be provided representing the target and distracter sounds (i.e. sound origins having configurable azimuthal directions between 0-360° and configurable elevation directions between −90°–90° relative to a horizontal reference plane, for example at the center of the user's head).

In this embodiment, the loudness of the variable target and distracter sounds are a function of the distance between the user's current location on the grid and the location of the target or distracter sounds. With increasing distance resulting in a softer sound and in reducing distance resulting in an increased or louder sound volume. In this embodiment, the user's orientation on the grid and relative to the auditory space is fixed such that they imagine always facing the same way if they were on the horizontal grid regardless of how they navigate or move around the grid.

At each user location on the grid, an arrangement of audio cues will be presented to the user over the audio delivery devices. The audio cues will at least include the target sound and additionally one or more distracter sounds whether fixed or variable in type. The number of target sounds and distracter sounds can be varied depending on the game level difficulty, with more distracter sounds being provided for levels of harder difficulty.

As the user moves from one grid location to the next grid location, the game machine in accordance with the game scenario reconfigures the arrangement of audio cues to reflect the any new loudness or direction values. Each audio cue arrangement may comprise a combination of the target and distracter sounds which may be played in a timed sequence or overlapping or continuous. The sequence may be played any number of one or more times while the user is at a particular location or may be in a continuous loop. It will be appreciated that the reconfiguration of the arrangement of audio cues at each new user location will depend on the relative direction and distance between each of the 'variable' target sounds and distracter sounds relative to the user in the new location, and loudness and direction localization for the audio sound may be adjusted accordingly as required. For example, as the user moves to a new location, all sounds being closer to the user will increase in volume while the sounds located further away from the user will decrease, and additionally the direction at which the virtual sounds are presented to the user will alter, if necessary, to correspond to the closest approximate azimuth direction (e.g. 0, 45, 90, 135, 180, 225, 270 and 315 degrees).

In this embodiment, the loudness of the target sound is calculated by the distance between the target sound and current player position with 1 block steps corresponding to +/−1 dB. In this embodiment, the terrain grid consists of 11×11 blocks so the maximum distance is 14.14 which equals 14.14 dB when the target sound (TS) and player are at diagonal corners.

Depending on the game difficulty and level, the distracter sounds may be constantly represented in the audio cue arrangements between each user move or may randomly or arbitrarily appear or disappear between successive audio cue arrangements. For example, the one or more distracter sounds may be constant in the arrangement of audio cues for each new move or may be arbitrarily present in one or more of the audio arrangements either alone or in combination with other distracter sounds.

Figure 9:
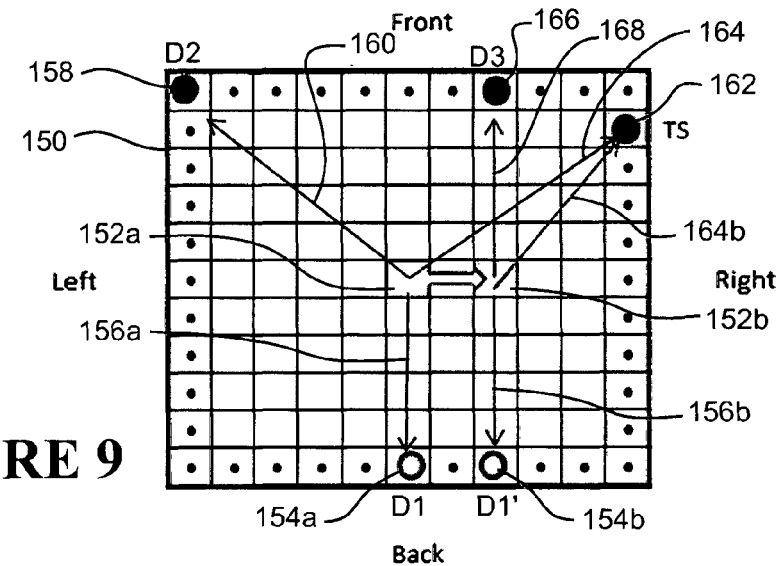
FIG. 9 shows a representation of the modification of the arrangement of audio cues in the terrain game scenario as the user navigates the terrain via the user interface.

Referring to FIG. 9, an example of the game scenario in use is shown. The terrain grid at the start of the game is shown at 150 (which is not visible to the user but which they must visualize or imagine). As shown, each wall of the outer peripheral wall of the grid represents a side of the user's head, with the left and right sides representing the left and right ears and front and back representing the front of the head and back of the head. The user's start position is at 152a. In this game scenario, the user is presented with an audio arrangement consisting of a fixed distracter sound D1 shown at 154a which is stimuli at the user's perceived tinnitus pitch (and possibly other sound attributes) and the user's perceived tinnitus location relative to the horizontal grid. In this case, the user has a tinnitus located in the center of the back of their head and this is represented by D1 being located and presented to the user over the audio delivery devices at an azimuthal direction of 180° as shown by arrow 156. The loudness of D1 is proportional to the distance between the player position 152a and location of D1 at 154a. In this case, D1 is a 'fixed' distracter sound in that its direction and loudness are fixed regardless of the user's position.

Another distracter sound D2 is located at 158 and originates at a directional location of 315° relative to the user's position as shown by arrow 160. Again, the loudness of D2 is proportional to the distance between the user position at 152a and D2 on the grid. D2 may have a pitch related to the user's perceived tinnitus characteristic or other corresponding sound characteristics. The target sound is located at 162 and its initial direction relative to the user is approximately 45° as shown by arrow 164 and again the loudness is dictated by the length of arrow 164. In this case, the user decides to move 2 grid blocks to the right in the first move as shown at 152b and this moves them closer to the target sound TS resulting in a smaller arrow 164b and therefore a louder target sound in the next audio cue arrangement. As for 'fixed' distracter sound D1 at the tinnitus location, its position is shown at 154b and maintains a fixed azimuth at 180° and the loudness is represented by arrow 156b as previously described. In this scenario, distracter sound D2 at 158 disappeared upon the user's move but is replaced by a new distracter sound D3 located at position 166 at an azimuth of 0° and loudness represented by the length of arrow 168. It will be appreciated that had the distracter sound D2 been a constant throughout the user's movements, it would have a loudness and direction that vary much like that of the target sound relative to the user's new position.

In this embodiment, the game scenario has 4 levels, but this may be varied in other embodiments. Level 1 is a training level in which only a target sound (TS) is present so that the user becomes familiar with that sound. In Level 2, TS is present, and fixed distractor D1 is added at the tinnitus location, along with variable distractor D2. In Level 3, another variable distractor D3 is added, and in Level 4 a further variable distractor D4 is added (not shown). The variable distracters D2-D4 may have a constant grid location as the user moves, or alternatively have random locations that alter for each user move. The audio cue arrangement after each user move is updated to reflect the terrain landscape regarding the user, target sound, and distractor sound locations.

Figure 10:
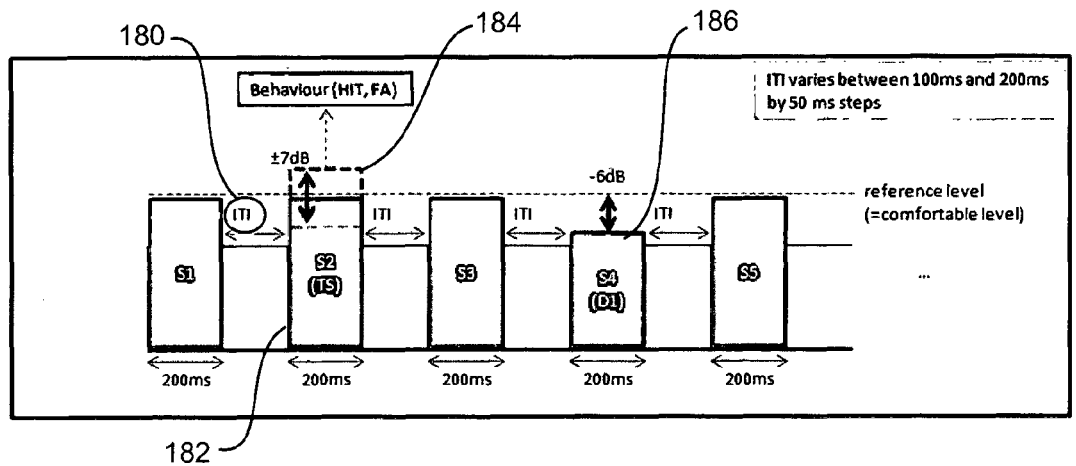
FIG. 10 shows a representation of a portion of the playback timeline of an audio cue arrangement of the terrain game scenario in accordance with an embodiment of the invention.

Referring to FIG. 10, an example of a portion of the playback timeline of an audio cue arrangement for the first start position of the user at 152 is shown. As shown, a sequence of pulsed stimuli is presented to the user over the audio delivery devices by the game machine in accordance with the game scenario. The stimuli (S1-S5) may be background noise or other sounds, the target sound and one or more distracter sounds. The interval between the stimuli shown at 180 may be constant or varied depending on difficulty, a longer interval for a lower difficulty or a shorter interval for a higher difficulty. In other situations, the presentation of stimuli may be continuous one after the other with no interval or alternatively the stimuli may be mixed such that they overlap for further increased difficulty. In this case, the target sound is presented at S2 as shown at 182 in the timeline of the audio arrangement. In this embodiment, the volume of the target sound 184 varies depending on the user's location relative to the target sound based on the loudness function as previously described. The distracter sound D1 is presented at S4 at 186 in the playback timeline and is presented in a fixed direction and loudness level. The stimuli S1, S3, and S5 may be any of either D2, D3, or D4 for example.

Stimuli Characteristics

In the example, the stimuli may have the following characteristics:

Loudness:
  Target stimulus (TS)—Comfortable level ±7 dB
  Tinnitus distracter (D1)—Comfortable level −6 dB
  Other distracters (D2-D4)—Comfortable level
  Where comfort level is set by user's initial loudness calibration Pitch:
The pitch rule has 3 options—1:octave difference, 2:JND (Just Noticeable Difference) difference, 3 fixed values. The default options is octave difference (⅓ octave).
  TS: Tinnitus pitch ($f_T$)—2 octave low
  D1: Tinnitus pitch ($f_T$)
  D2: Tinnitus pitch ($f_T$)—1 octave low
  D3: Tinnitus pitch ($f_T$)—3 octave low
  D4: Tinnitus pitch ($f_T$)—4 octave low Bandwidth: 1 octave narrowband noise Localization—The directions of stimuli are randomly determined in a horizontal plane (0 45 90 135 180 225 270 315 azimuth) but D1 is at a fixed location at any game level. If participant has a tinnitus in a centre position of the head, D1 is located at 180 (back of head).

Time course—All stimuli are randomly ordered and generated with fixed interval (ITI). The order and ITI are relocated when participant moves.

It will be appreciated that the stimuli characteristics above may be altered depending on the game scenario.

It will be appreciated that the proportion of the audio arrangement sequence in which the target sounds and/or distracter sounds are presented may be varied depending on difficulty level of the game scenario. For example, the target sound may be present for 100% of the sequence where there are no distracter sounds, or for a lesser proportion as one or more distracter sounds are introduced into the audio arrangement to increase difficulty. As previously discussed, the audio cue arrangement may have a looping repetition of the same sequence or alternatively the sequence of target and distracter sounds may be randomly generated into the sequence.

During the performance, various data may be measured and stored during the user's interaction with the game. For example, a hit or miss score may be generated for each user move where a hit indicating a move closer to the target sound and a miss indicating a move further away from the target sound. Likewise, the response time between each move may be recorded. Additionally, the score may increment as the treasures are collected in the game. The final score may be determined at the end of a preset gameplay time, such as 30 minutes. The levels of difficulty may increase at the predetermined score levels or upon collection of a predetermined number of treasures or upon the collection of each treasure may initiate a new level.

3. Example 2—Sound Categorization or Discrimination Game Scenario—Submarine Game With reference to FIGS. 11-13, an example of one type of game scenario configured to provide categorization training (CT) and/or discrimination training (DT) will be described in the context of frequency categorization training (FCT) and frequency discrimination training (FDT). DT teaches users to differentiate between similar sounds while CT teaches users to identify stimuli within a particular frequency range as members of the same category. DT leads to increased sensitivity and greater cortical representation. CT leads to a decrease in sensitivity and reduced cortical representation. Such training aims to reduce tinnitus through plastic modification of the cortical representation of tinnitus pitch.

In this game scenario, the audio cue arrangements may comprise a combination or one or more target sounds and one or more distractor sounds. The sound characteristics of each sound are configured based on one or more sound characteristics of the tinnitus as perceived by the user, and the game machine is configured to advance the user in the game scenario in response to user feedback indicative of the user correctly categorizing target and distractor sounds or discriminating between the target and distractor sounds.

In this example, the game scenario is called the submarine game and it runs on the interactive gaming system previously described. Like the terrain game, the submarine game includes a game customization phase for configuring the game scenario to the individual user and their perceived tinnitus characteristics, and this process has been previously described. In this example, the game scenario is switchable between FCT and FDT modes, although it will be appreciated that game scenarios dedicated to either FCT or FDT may be provided in alternative embodiments. Depending on which training mode is selected, the sound characteristics of the target and distractor sounds are configured accordingly based on the user's tinnitus profile.

In this game scenario, the user is to imagine that they are a submarine and are guarding their territorial waters in the dark sea from enemies. The user is required to listen to the arrangement of audio cues to find and shoot the enemies (target sounds), but not shoot friendly submarines (distractor sounds). The audio cues may be quiet at first but moving into the user's 3D auditory space three-dimensionally. The user's fuel tank is limited so they must complete their mission with a predetermined time limit.

The user has two ways to find enemies, using passive sonar and active sonar. Passive sonar is a ping (audio cue) from an enemy who wants to find the user. The user should shoot as soon as they hear the enemy submarine (target sound) over the audio delivery devices, otherwise they are shot by the enemy. Active sonar is a ping from the user to find the enemy and it will be returned as same or similar sound if they are present. The user should shoot as soon as they hear the ping (target sound) otherwise they are shot by the enemy. The number of active sonar pings are limited because this sonar is a risky means for the user, as it assists the enemy to find the user too. The passive sonar and active sonar audio cues sound the same or similar.

The number of enemy is known and is displayed to the user as well as their fuel tank level (remaining time) on a display screen associated with the game machine.

In this embodiment, the game scenario has 4 levels. In level 1, the user can't see the enemies. As the user hears a passive sonar (target sound), they should shoot it via operation of the user interface. In this example, the user interface may be a numeric keyboard and shooting in this level is enabled by pressing 1. In this level the user gets familiar with passive sonar sounds=enemy submarine sounds (target sounds).

In level 2, it is similar to level 1 except the audio cue arrangement comprises a target sound (enemy submarine) and a distractor sound that is designed to distract the user. The distractor sound is in the form of a friendly submarine that sound similar to the enemy submarine but isn't the same. The user needs to discriminate (or categorize) the two successive sounds and shoot what they think is the enemy submarine. The user can select which sound in the audio cue arrangement by pressing the number on the keypad corresponding to which sound they think is the enemy submarine. For example, if the user thinks it was the first sound, they press 1, but they press 2 if they think it was the second sound in the audio cue arrangement. In this level the user gets familiar with friendly submarine sounds (distracter sounds). As explained above, the audio cue arrangements are triggered to playback either in response to the activation of an active sonar by the user via the user interface, or alternatively predetermined timing controlled by the game scenario (e.g. passive sonar).

Level 3 is the same as Level 2, but there are more distracters (friendly submarines). The audio cue arrangements comprise three sonars that arrive sequentially. The user must again discriminate (or categorize) them and then shoot enemy submarine (press 1 or 2 or 3). Level 4 is the same as Level 3 but there are more distracters again (friendly submarines). Four sonars come sequentially. The user must again discriminate (or categorize) them and shoot the enemy submarine (press 1 or 2 or 3 or 4).

It will be appreciated that the audio cue arrangements may be configured to have more than one enemy submarines (target sounds) to shoot in other embodiments.

Figure 13:
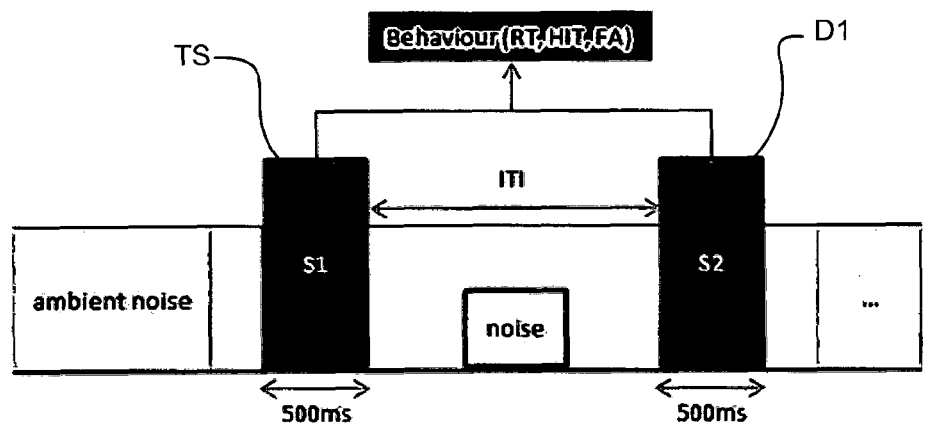
FIG. 13 shows a representation of a portion of the playback timeline of an audio cue arrangement of the submarine game scenario in accordance with an embodiment of the invention.

Referring to FIG. 13, an example playback timeline of an audio cue arrangement at level 2 is shown with stimuli 1 (S1) followed sequentially after an interval (ITI) by stimuli 2 (S2). The duration of the stimuli and interval may be varied as desired. In this case, the target sound (TS) is S1, and the distractor sound (D1) is S2. To score points or progress, the user should respond by shooting S1, i.e. by pressing 1. In this example, ambient noise or sounds (for example broadband noise like sea waves) may be provided continuously in the background during gameplay to avoid tinnitus recall by user due to quiet.

The game scenario may provide the user with audible, visual or tactile feedback after each shot as to whether they were successful in shooting the enemy submarines, and none of their own friendly submarines.

As with the terrain game, the user's performance data, including level progression, response time, hits, misses, score and the like are stored in memory for later use.

Stimuli Characteristics

In the example, the stimuli may have the following characteristics:

Loudness—all stimuli loudness at comfortable level

Pitch

There are two game modes—FCT and FDT. A JND measurement mode may be included before the gaming.

Figure 11:
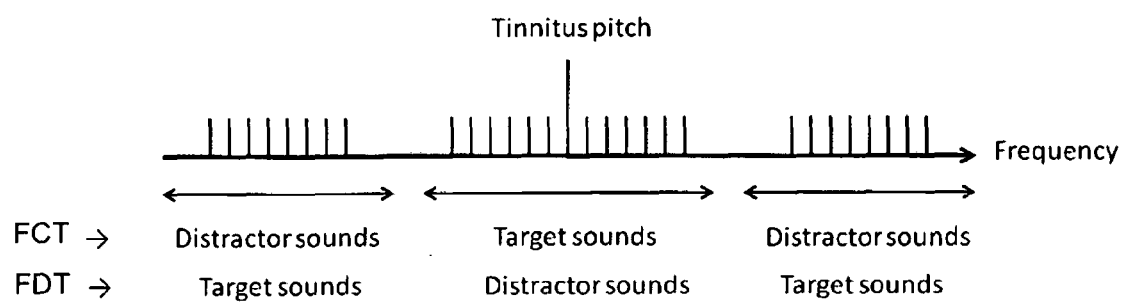
FIG. 11 shows a representation of the frequency characteristics of target sounds and distracter sounds used in the interactive gaming system in a 'submarine' game scenario in accordance with an embodiment of the invention.

FCT (Frequency categorization training)—see FIG. 11

Target sounds—tones at tinnitus pitch and surrounding tones

Distracter sounds—tones suitably different in frequency from the target sounds

FDT (Frequency discrimination training)—see FIG. 11

Target sounds—tones suitably different in frequency from tinnitus pitch

Distracter sounds—tones around the target sounds including the tinnitus pitch

Bandwidth: Narrowband noise

Location

Figure 12:
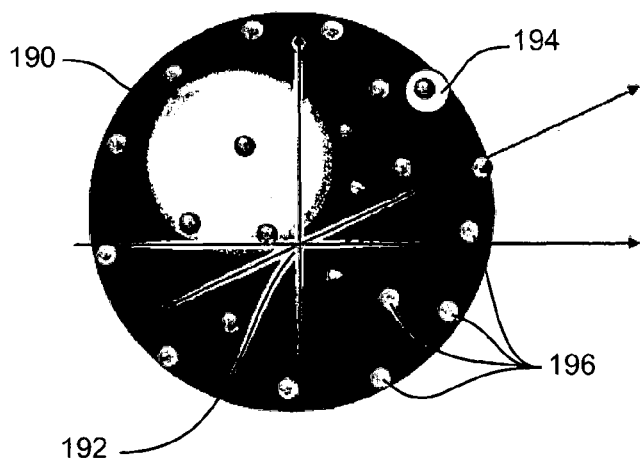
FIG. 12 shows a representation of the 3D auditory space and various possible locations of distracter sounds and target sounds in the submarine game scenario in accordance with an embodiment of the invention.

FIG. 12 shows an example of the 3D auditory space relative to the center of the user's head 192. In this example, the stimuli (target and distractor sounds) may be presented to the user so as to appear to originate from a range of directions in 3D auditory space. For example, in this configuration sound locations are at 3D—0 45 90 135 180 225 270 315 azimuth and −60 −30 0 −30 60 elevation, so maximum 40 points or available sound locations 196 from which the target and distractor sounds may appear to originate. In this example, both target sounds and distracter sounds locations randomly selected from these available 3D locations 196. Over a long term average, this means that 1 in 40 sounds are likely to come from user's tinnitus location 194.

Training Program

In the example, the submarine game may be played according to the following training program:

Response Times, and Hits and Misses recorded for each level

Each level will be over once time limit reached (30 minutes).

The game difficulty increases after the user gets 3 successive hits AND minimum days at each level. The minimum days are, LEVEL 1—1 day LEVEL 2—2 days LEVEL 3—3 days The training will be halted in 10 days.

4. Clinical Trial—Experimental Results

A summary of the experimental results from a clinical trial carried out with an implementation of the interactive gaming system in the form of the sound localisation Terrain game scenario of example 1 will now be described with reference to FIGS. 14A-19. The experimental results described are by way of example only to demonstrate benefits of the interactive gaming system in one embodiment and the explanation is not intended to be limiting. The various clinical assessment criteria and measurement techniques and data will be appreciated by those skilled in audiology.

Hypothesis of Clinical Trial

The hypothesis of the clinical trial was that auditory training using, for example, the Terrain game implementation of interactive gaming system of the invention would change a user's tinnitus perception compared to a non-auditory (for example visual) control game such as Tetris.

Participants in Clinical Trial

Adult participants, with hearing loss and tinnitus were sought. Hearing loss was defined as hearing thresholds: >20 dB HL, for 250 Hz to 8 kHz. Those planning to participate were instructed the study required audiometric & tinnitus assessment, questionnaire provision covering cognitive stage, depression, anxiety, stress and tinnitus impressions, and would involve and engagement in a computerised, take-home auditory or visual perceptual training programme (depending on group randomised to) for 30 minutes per day, for 20 consecutive days. Compatibility of potential participant's home computer systems was confirmed to ensure a) availability—access to a home computer and b) compatibility—the home computer would work well with the Terrain or Tetris programmes.

Potential participants were informed that there would be four, primary sessions of data collection: 2 sessions prior to the computerised perceptual training and 2 sessions post-training. The participants were randomly assigned (without conterbalancing for any demographic factors) into two groups. Fifteen participants were assigned to a group to receive the Terrain game auditory attention task, being referred to as the 'Terrain group'. Sixteen participants were randomly assigned to an active control group to receive the Tetris game visual attention task, being referred to as the 'Tetris group'. All participants were assessed according to psychometric and questionnaire assessment criteria.

Those volunteers demonstrating hearing pathology or insufficient tinnitus complaint were excluded from the study. Participants with severe or greater (>70 dB HL) hearing loss for the subjective tinnitus pitch-match frequency and octave side-bands and those demonstrating difficulty with hearing the perceptual training stimuli during a demonstration session, were excluded as training and data collection stimuli would potentially be inaudible. Individuals with significant asymmetrical hearing: difference of >15 dB HL in pure-tone thresholds for three, identical speech-dominant frequencies when comparing between ears were also be excluded to ensure participants would hear the binaural stimuli associated with some of the CAB® tests.

The mean age of participants in the Terrain group was 52.33 years, (range=22-66, standard deviation=10.61). Twelve participants were male and three were female. Participant handedness revealed 1 was left-handed and 14 were right-handed. Eight individuals reported musicianship: mean number of years of musical study=7.38, (range=2 to 30 years, standard deviation=9.23). Pure-tone threshold mean (250-8000 Hz) was 20.42, (range=0-55 dB HL, standard deviation=11.01) for the right ears and 23.83, (range=0-75, standard deviation=15.99) for the left ears. Three participants reported that they were multilingual.

The mean age of participants in the Tetris group was 62.25 years, (range=52-69 years, standard deviation=4.64). Nine participants were male and seven were female. Participant handedness revealed 1 with left-handed and 15 with right-handed partiality. Six participants indicated musicianship: mean number of years of musical study=6.00, (range=2-10 years, standard deviation=2.76). Pure-tone thresholds mean (250-8000 Hz) was 28.95, (range=0-80, standard deviation=13.88) for the right ears and mean 30.20, (range 0-95, standard deviation=14.65) for the left ears. One participant indicated they were multilingual.

Assessments and 20-day Gameplay/Training

All participants underwent audiometric and tympanometric assessment and were administered an SSQ questionnaire. All participants recruited had hearing loss and tinnitus and received psychometric tinnitus assessment: tF, tLM and MMLs, as well as questionnaires: TSCHQ, THI and TSNS. The primary outcome measure was the TFI. Some of the assessments were performed both before and after the 20-day game training.

The Terrain group were instructed to play the interactive, computerised auditory perception training game called 'Terrain' as described generally with reference to example 1 above. The Tetris group were instructed to play a visual-only gaming counterpart to the auditory-only perceptual training, (based on the classic Tetris interlocking puzzle game (Pajitnov, 1984)) which was engineered using LabVIEW™ 8 (National Instruments, 2005). The software was designed to have the same look and pre-training calibration as the Terrain game.

Participants received instruction regarding the loading of the perceptual game to their personal computer systems, game operation/play and objectives. Both Terrain and Tetris games were programmed to provide training for 20 consecutive days, for 30-minutes per day. This version of the game could be paused to provide a break in play in needed, but would not advance to the next day of play, until 30 minutes of gaming had elapsed. Participants were signalled via an automated pop-up when the 30 minutes of training had concluded.

Results—Terrain Group

Figure 14A:
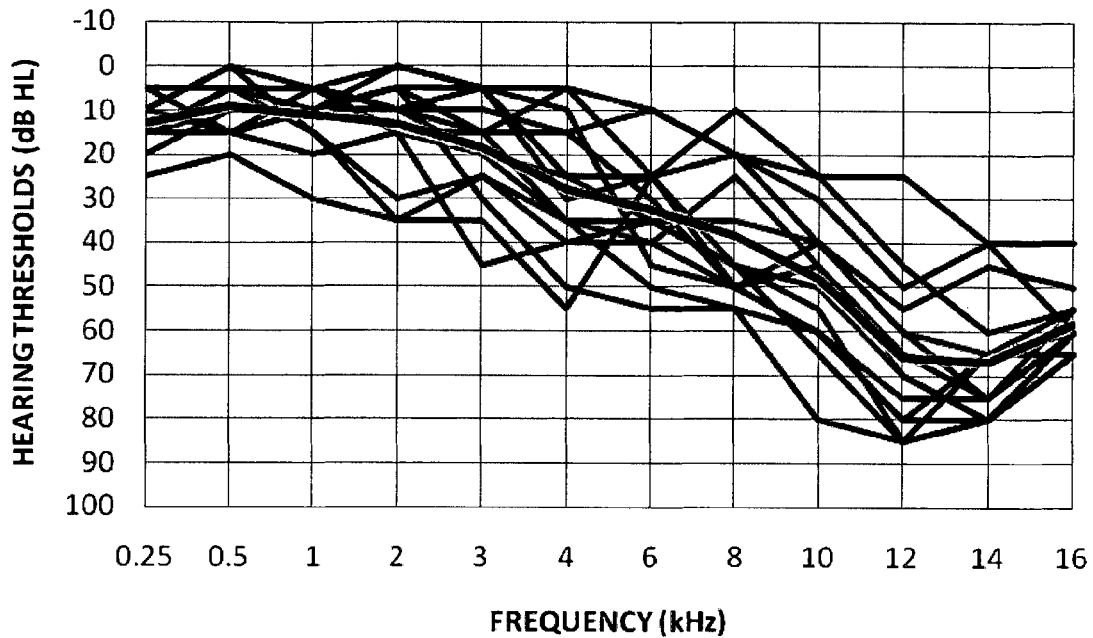
FIGS. 14A and 14B show graphs of the mean and individual audiometric thresholds for participants right and left ears respectively for a 'Terrain group' in a clinical trial involving an embodiment of the invention.
Figure 14B:
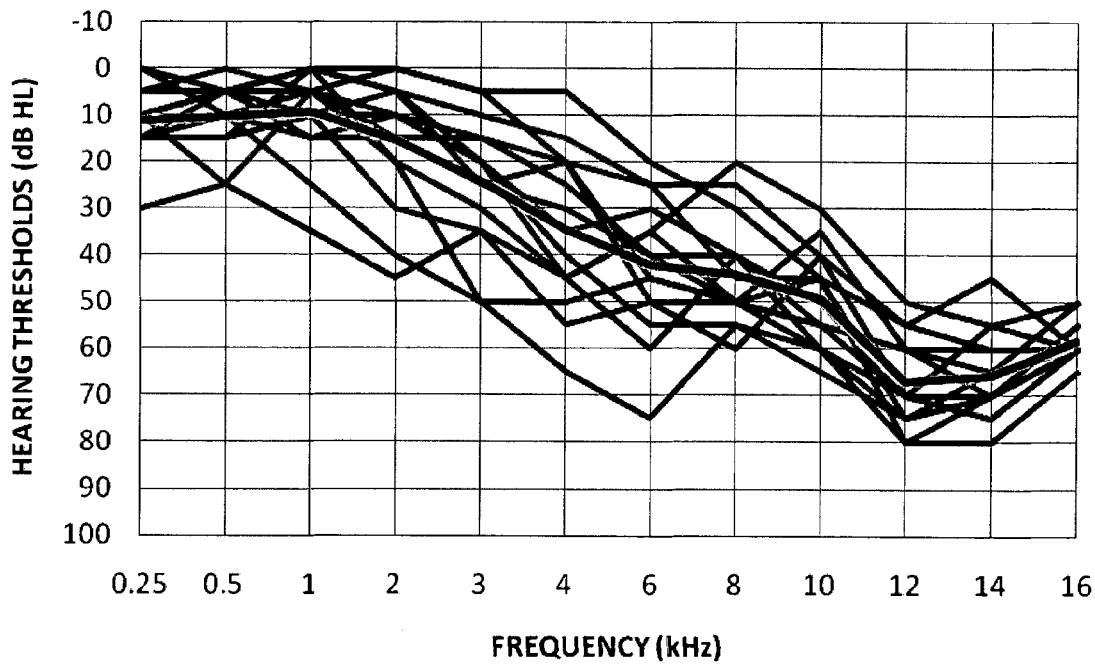

FIGS. 14A and 14B show the mean and individual audiometric threshold for participants in the Terrain group.

Table 1 below shows the mean data from the Terrain group for the questionnaire assessment, including Depression Anxiety Stress Scale (DASS), Mini Mental State Exam (MMSE), Coping Scale for Adults (CSFA), Speech Spatial Qualities (SSQ), Tinnitus Sample Case History Questionnaire (TSCHQ) and subjective Tinnitus Tester pitch-match (Ft).

TABLE 1

| EVALUATION COMPONENTS | Mean | Range | SD |
|---|---|---|---|
| DASS | 6.10 | (0-18) | 6.04 |
| MMSE | 29.8 | (29-30) | 0.41 |
| CSFA-Deal with Problem Style | 56.8 | (18-78) | 16.33 |
| CSFA-Non-coping Style | 44.87 | (16-66) | 14.13 |
| CSFA-Optimism Style | 44.33 | (10-80) | 21.37 |
| CSFA-Sharing Style | 56.67 | (10-130) | 29.20 |
| SSQ-Speech Hearing | 103.80 | (64-140) | 23.17 |
| SSQ-Spatial Rating | 141.40 | (101-170) | 22.01 |
| SSQ-Sound Qualities | 141.20 | (16-180) | 41.19 |
| TSCHQ-Tinnitus Duration (years) | 5.67 | (.5-30) | 8.64 |
| TSCHQ-Tinnitus Loudness/100 | 50.40 | (18-80) | 20.88 |
| TSCHQ-% Time Annoyed | 21.40 | (1-50) | 18.67 |
| Tinnitus Tester-Ft (kHz) | 7.75 | (3-12) | 3.28 |

Table 2 below shows the mean data from the behavioural assessment for the Terrain group collected at two time periods: Time 1=before game training and Time 2 is post game training, including assessments of Minimum Masking Levels (MMLs) for right (R) and left (L) ears respectively, for frequencies: 500 Hz, 1000 Hz, 2000 Hz, 4000 Hz and tinnitus pitch-match (Ft), using narrow-band noise. Table 2 also shows the mean data from the Clinical Global Improvement (CGI) questionnaire administered at two time periods to the Terrain group: Time 1=post game training and Time 2=three weeks post-training.

TABLE 2

| EVALUATION COMPONENTS | TIME 1 Mean | Range | SD | TIME 2 Mean | Range | SD |
|---|---|---|---|---|---|---|
| MML dB SL, 500 Hz, (R) | 11.80 | (3-33) | 9.84 | 11.00 | (0-25) | 7.23 |
| MML dB SL, 1000 Hz, (R) | 11.33 | (2-40) | 10.38 | 10.53 | (0-26) | 7.59 |
| MML dB SL, 2000 Hz, (R) | 12.07 | (2-30) | 8.39 | 10.27 | (0-26) | 6.95 |
| MML dB SL, 4000 Hz, (R) | 9.27 | (2-30) | 8.13 | 12.13 | (0-43) | 11.02 |
| MML dB SL, Ft, (R) | 9.67 | (1-24) | 7.97 | 9.27 | (0-23) | 6.67 |
| MML dB SL, 500 Hz, (L) | 12.93 | (1-41) | 11.30 | 15.73 | (0-43) | 11.15 |
| MML dB SL, 1000 Hz, (L) | 12.8 | (2-41) | 10.16 | 14.53 | (0-51) | 12.45 |
| MML dB SL, 2000 Hz, (L) | 12.2 | (2-43) | 10.19 | 13.33 | (0-34) | 10.08 |
| MML dB SL, 4000 Hz, (L) | 9.60 | (3-21) | 6.43 | 11.80 | (0-34) | 9.53 |
| MML dB SL, Ft, (L) | 8.47 | (1-25) | 8.17 | 9.47 | (0-21) | 7.38 |
| CGI | 3.10 | (1-4) | 0.93 | 2.93 | (1-4) | 0.82 |

Table 3 below shows the mean data from the questionnaire assessment for the Terrain group collected at four time periods: Time 1=baseline prior to game training, Time 2=prior to game training, Time 3=post-game training, and Time 4=three weeks post-training. Assessments include Tinnitus Functional Index (TFI), Tinnitus Handicap Index (THI), Severity Numeric Scale (TSNS) and Attention and Performance Self Assessment (APSA).

TABLE 3

| EVALUATION COMPONENTS | TIME 1 Mean | Range | SD | TIME 2 Mean | Range | SD | TIME 3 Mean | Range | SD | TIME 4 Mean | Range | SD |
|---|---|---|---|---|---|---|---|---|---|---|---|---|
| TFI | 30.67 | (0-60) | 17.09 | 26.67 | (0-50) | 12.91 | 15.33 | (0-50) | 13.56 | 15.33 | (0-50) | 14.57 |
| THI | 25.53 | (0-60) | 16.01 | 25.27 | (2-60) | 14.87 | 19.07 | (0-48) | 13.69 | 16.60 | (0-59) | 13.92 |
| TSNS-Problem | 2.73 | (2-4) | 0.70 | 2.60 | (2-4) | 0.63 | 2.20 | (1-4) | 0.86 | 2.20 | (1-5) | 1.08 |
| TSNS-Loudness | 4.80 | (2-7) | 1.90 | 4.73 | (2-7) | 1.79 | 3.80 | (1-7) | 1.78 | 4.17 | (2-7) | 2.17 |
| TSNS-Uncomfortable | 4.87 | (1-8) | 2.26 | 4.67 | (2-8) | 1.95 | 3.47 | (1-7) | 2.17 | 3.10 | (1-9) | 2.30 |
| TSNS-Annoying | 4.93 | (2-8) | 1.75 | 4.80 | (2-8) | 2.08 | 3.67 | (1-8) | 2.19 | 3.07 | (1-7) | 1.94 |
| TSNS-Ignore | 6.13 | (2-10) | 2.67 | 5.67 | (1-10) | 2.81 | 3.47 | (1-8) | 1.92 | 3.40 | (1-7) | 1.84 |
| TSNS-Unpleasant | 5.20 | (3-7) | 1.57 | 4.80 | (2-7) | 1.52 | 3.40 | (2-7) | 1.64 | 3.00 | (2-7) | 1.81 |
| APSA | 1.13 | (0-2) | 0.74 | 1.27 | (0-2) | 0.70 | 1.00 | (0-2) | 0.53 | 0.87 | (0-2) | 0.74 |

Figure 15A:
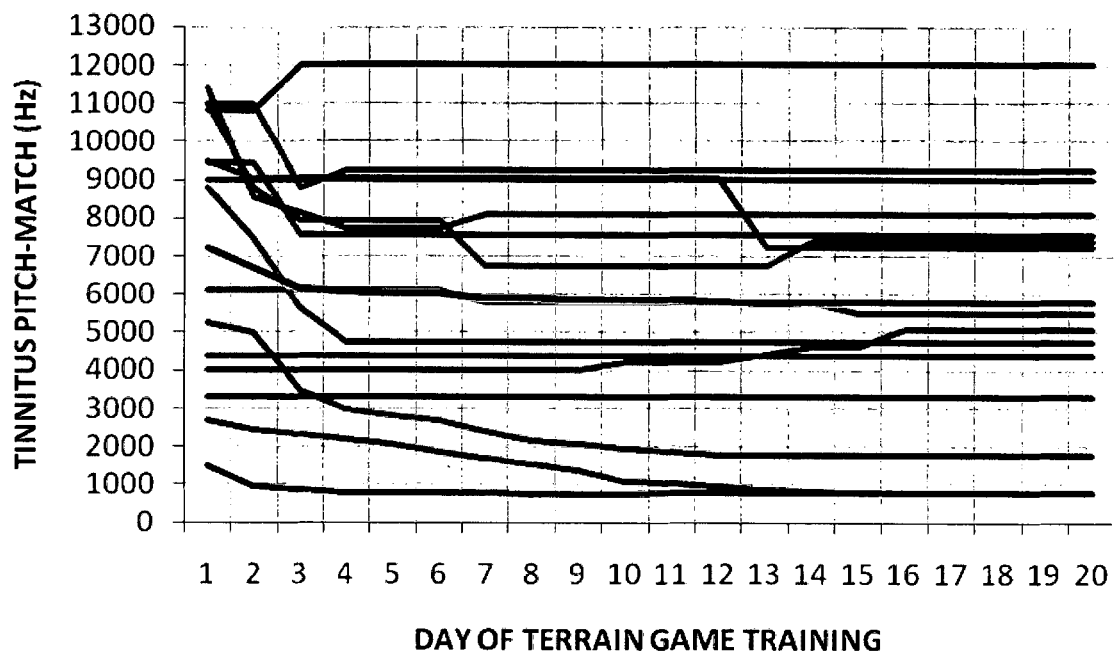
FIG. 15A shows a graph of the mean and individual change in subjective tinnitus pitch-match for participants in the clinical trial for the Terrain group.
Figure 15B:
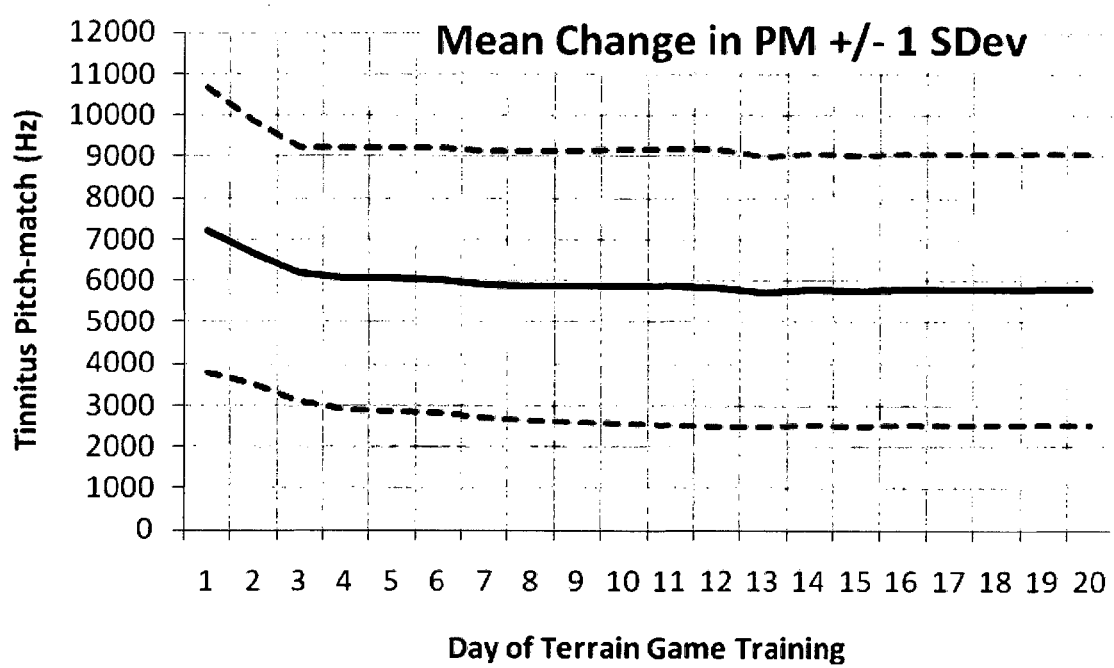
Figure 16A:
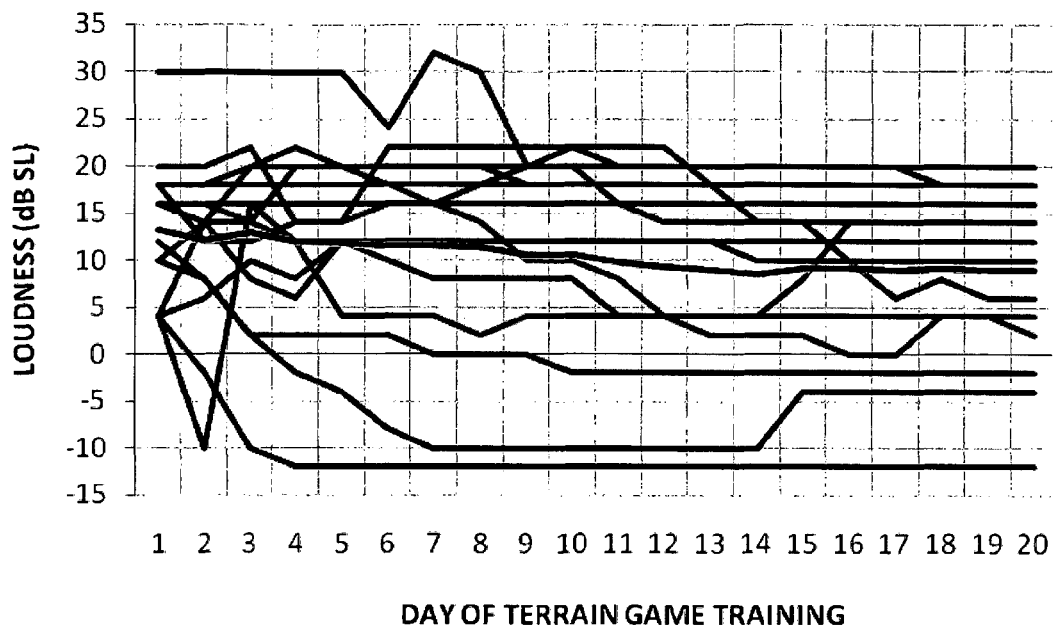
FIG. 16A shows a graph of the mean and individual subjective change in tinnitus loudness (dB SL) for 3D tinnitus sound-match for participants in the clinical trial for the Terrain group.
Figure 16B:
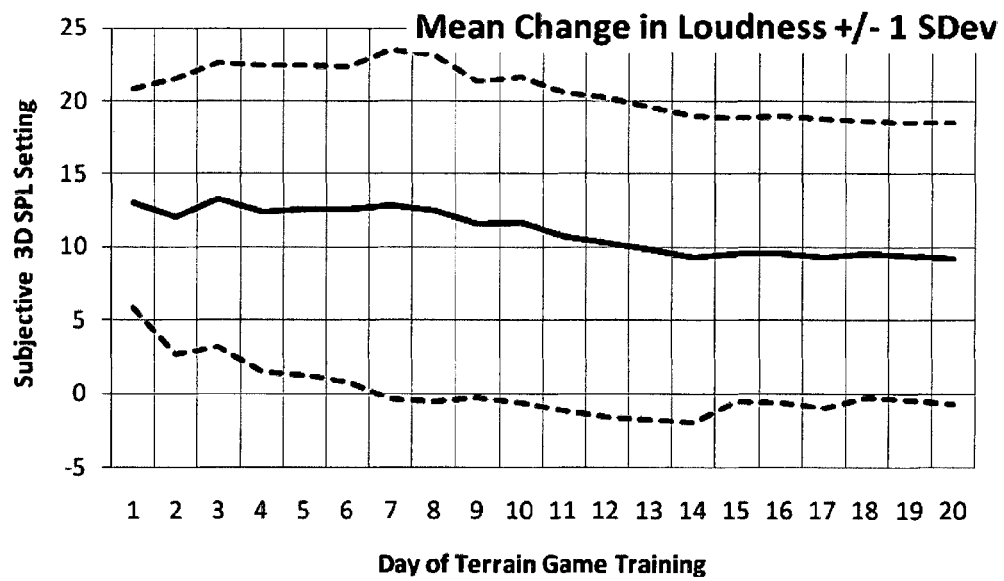
FIG. 16B shows a graph of the mean subjective change in tinnitus loudness of FIG. 16A with reference to +/−one standard deviation for the Terrain group.

Referring to FIGS. 15A and 15B, the data collected from the Terrain game during the daily tinnitus calibration function prior to gameplay revealed a mean tinnitus pitch-match of 7213.33 Hz and this trended downward at approximately day 3 of Terrain game training and remained at this lower frequency (approximately 6000 Hz) for the remainder of the 20 day game training. Likewise, referring to FIGS. 16A and 16B, the data collected from the Terrain game daily tinnitus calibration function revealed downwardly trending mean tinnitus loudness over the 20-day clinical trial of game training.

Results—Tetris Group

Figure 17A:
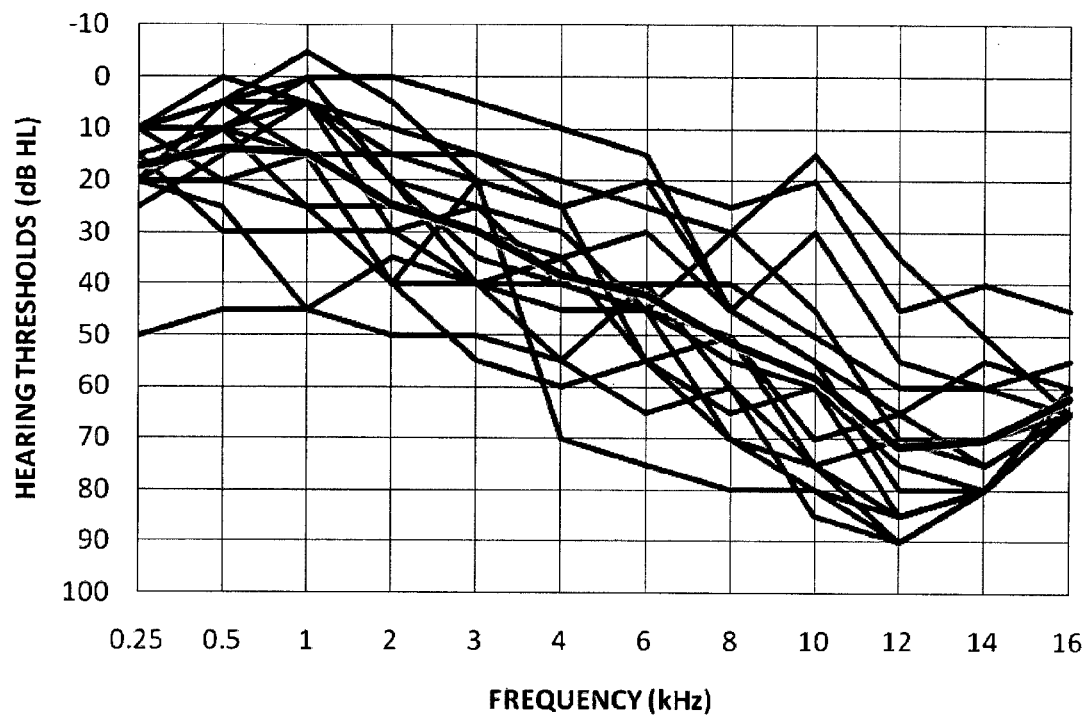
FIGS. 17A and 17B show graphs of the mean and individual audiometric thresholds for participants right and left ears respectively for a 'Tetris group' in a clinical trial involving an embodiment of the invention.
Figure 17B:
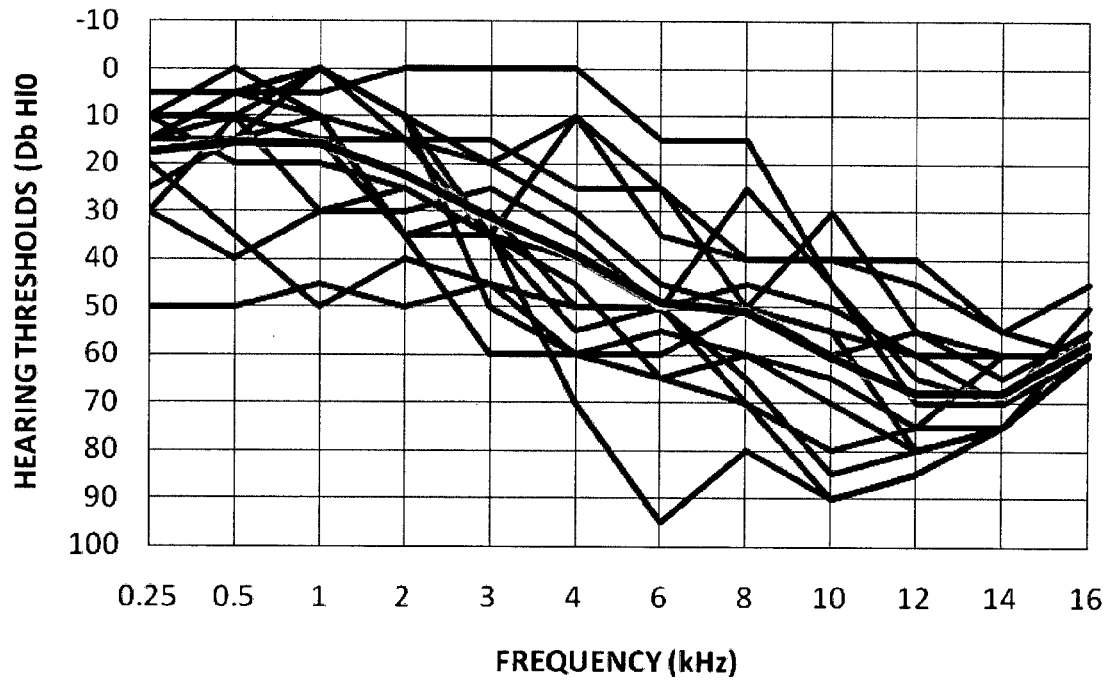

FIGS. 17A and 17B show the mean and individual audiometric threshold for participants in the Tetris group. Tables 4-6 show the equivalent data to Tables 1-3 for the participants from the Tetris group.

TABLE 4

| EVALUATION COMPONENTS | Mean | Range | SD |
|---|---|---|---|
| DASS | 1.88 | (0-13) | 3.69 |
| MMSE | 29.5 | (29-30) | 0.63 |
| CSFA-Deal with Problem Style | 68.44 | (36-90) | 12.83 |
| CSFA-Non-coping Style | 45.75 | (24-72) | 13.62 |
| CSFA-Optimism Style | 62.50 | (40-90) | 12.91 |
| CSFA-Sharing Style | 37.63 | (0-60) | 21.96 |
| SSQ-Speech Hearing | 80.81 | (20-131) | 36.47 |
| SSQ-Spatial Rating | 127.88 | (53-169) | 31.71 |
| SSQ-Sound Qualities | 139.78 | (69-177) | 33.79 |
| TSCHQ-Tinnitus Duration (years) | 16.00 | (1-50) | 12.72 |
| TSCHQ-Tinnitus Loudness/100 | 47.31 | (7-100) | 24.40 |
| TSCHQ-% Time Annoyed | 19.69 | (0-50) | 16.48 |
| Tinnitus Tester-Ft (kHz) | 7.48 | (2-13) | 3.01 |

TABLE 5

| EVALUATION COMPONENTS | TIME 1 Mean | Range | SD | TIME 2 Mean | Range | SD |
|---|---|---|---|---|---|---|
| MML dB SL, 500 Hz, (R) | 8.81 | (1-25) | 6.63 | 8.88 | (1-14) | 4.01 |
| MML dB SL, 1000 Hz, (R) | 8.31 | (2-23) | 5.80 | 6.00 | (0-14) | 3.20 |
| MML dB SL, 2000 Hz, (R) | 8.18 | (1-18) | 4.87 | 6.38 | (2-11) | 3.38 |
| MML dB SL, 4000 Hz, (R) | 6.06 | (1-18) | 4.67 | 5.93 | (1-11) | 3.04 |
| MML dB SL, Ft, (R) | 5.50 | (1-23) | 6.29 | 4.88 | (1-11) | 3.20 |
| MML dB SL, 500 Hz, (L) | 10.50 | (1-47) | 11.25 | 7.06 | (1-16) | 4.61 |
| MML dB SL, 1000 Hz, (L) | 10.94 | (2-44) | 10.71 | 7.75 | (1-15) | 4.37 |
| MML dB SL, 2000 Hz, (L) | 9.43 | (1-31) | 8.40 | 7.00 | (0-14) | 4.02 |
| MML dB SL, 4000 Hz, (L) | 8.56 | (1-23) | 7.41 | 6.06 | (0-14) | 4.34 |
| MML dB SL, Ft, (L) | 7.25 | (1-23) | 7.26 | 4.81 | (0-11) | 3.47 |
| CGI | 3.56 | (2-5) | 0.81 | 3.28 | (1-4) | 1.00 |

TABLE 6

| EVALUATION COMPONENTS | TIME 1 Mean | Range | SD | TIME 2 Mean | Range | SD | TIME 3 Mean | Range | SD | TIME 4 Mean | Range | SD |
|---|---|---|---|---|---|---|---|---|---|---|---|---|
| TFI | 25.63 | (0-70) | 17.11 | 26.88 | (0-60) | 18.15 | 21.25 | (0-60) | 20.29 | 19.38 | (0-50) | 16.92 |
| THI | 18.63 | (6-44) | 10.87 | 20.00 | (6-42) | 9.69 | 16.50 | (2-38) | 9.22 | 17.63 | (0-36) | 10.76 |
| TSNS-Problem | 2.57 | (2-4) | 0.73 | 2.56 | (2-5) | 0.81 | 2.25 | (1-4) | 0.77 | 2.19 | (1-3) | 0.75 |
| TSNS-Loudness | 5.13 | (3-10) | 2.28 | 4.81 | (1-10) | 2.64 | 4.63 | (2-9) | 2.33 | 4.38 | (2-8) | 2.16 |
| TSNS-Uncomfortable | 5.25 | (1-9) | 2.29 | 4.94 | (2-10) | 2.29 | 4.31 | (1-10) | 2.57 | 4.50 | (1-9) | 2.73 |
| TSNS-Annoying | 5.06 | (1-9) | 2.69 | 5.16 | (2-10) | 2.23 | 4.31 | (1-9) | 2.36 | 4.19 | (1-9) | 2.66 |
| TSNS-Ignore | 4.94 | (1-10) | 2.57 | 4.94 | (1-9) | 2.54 | 3.63 | (1-8) | 2.28 | 4.06 | (1-8) | 2.62 |
| TSNS-Unpleasant | 5.13 | (2-10) | 2.44 | 4.97 | (2-10) | 2.45 | 4.06 | (1-9) | 2.43 | 3.94 | (1-7) | 2.38 |
| APSA | 1.44 | (0-2) | 0.63 | 1.44 | (1-2) | 0.51 | 1.31 | (0-2) | 0.70 | 1.44 | (0-2) | 0.63 |

Results—Terrain Group Verses Tetris Group

Figure 18:
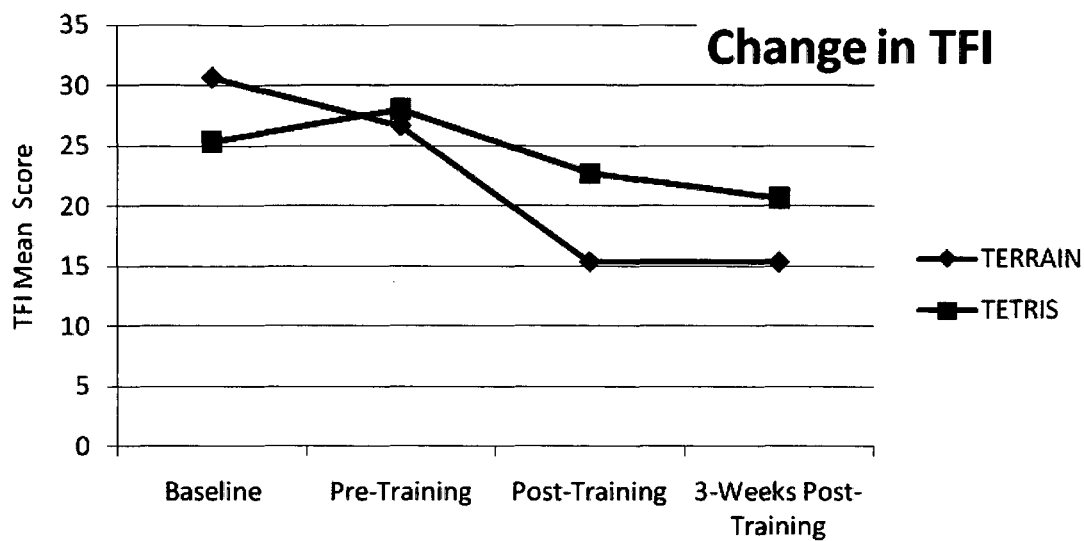
FIG. 18 shows a graph of the mean Tinnitus Functional Index (TFI) for the participants of the Terrain group and Tetris group in the clinical trial assessed at various times relative to the clinical trial.
Figure 19:
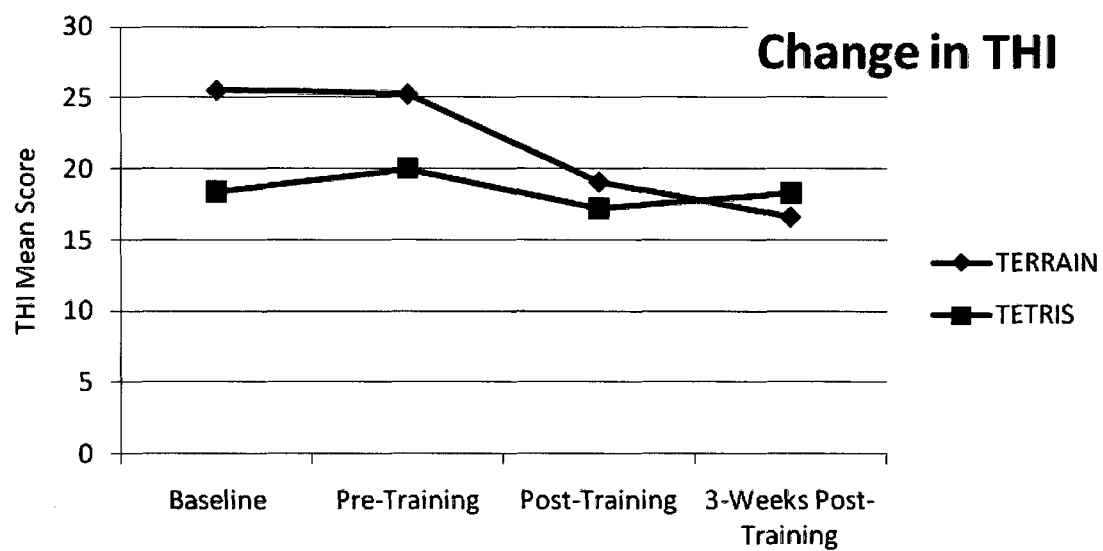
FIG. 19 shows a graph of the mean Tinnitus Handicap Index (THI) for the participants of the Terrain group and Tetris group in the clinical trial assessed at various times relative to the clinical trial.

Two quality of life measures were assessed for the Tetris group and Terrain group at four assessment times relative to the 20 day clinical training, namely baseline—three weeks prior to game training, immediately prior to game training, directly after 20 day game training, and three weeks after game training with no intervention. FIG. 18 shows the mean change in the Tinnitus Functional Index (TFI) for the Terrain and Tetris groups for the four assessment time and FIG. 19 shows the mean change in Tinnitus Handicap Index (THI) for the Terrain and Tetris groups over the four assessment times. As shown, participants training with the Terrain game show improvements in their Tinnitus quality of life factors, which is sustained for at least three weeks following the game training being stopped.

The foregoing description of the invention includes preferred forms thereof. Modifications may be made thereto without departing from the scope of the invention as defined by the accompanying claims.

The invention claimed is:

1. An interactive auditory training rehabilitation gaming system for a user suffering tinnitus comprising:
   an electronic game machine having a processor configured to provide a game scenario in which the user's performance in the game scenario is based on the user's response to audio cue arrangements comprising a combination of sounds, and where at least one of the sounds has one or more sound characteristics that are configured based on one or more sound characteristics of the user's perceived tinnitus, and wherein the sound characteristics of the user's perceived tinnitus comprises spatial attributes indicative of the spatial location in 3D auditory space of the sound source location of the tinnitus as perceived by the user;
   an audio delivery device or devices that are driven by the game machine to present the audio cue arrangements to the user in accordance with the game scenario; and
   a user interface in signal communication with the game machine and which is operable by a user to interact with the game scenario by responding to the audio cue arrangements.

2. An interactive gaming system according to claim 1 wherein the sound characteristics of the user's perceived tinnitus comprise any one or more of the following sound attributes:
   frequency, patch, bandwidth, loudness, temporal properties, or type of stimuli.

3. An interactive gaming system according to claim 1 wherein at least one audio cue arrangement comprises a sequential playback of sounds in accordance with a playback timeline.

4. An interactive gaming system according to claim 1 wherein the game machine is configured to present background noise or ambient sound constantly or intermittently over the audio delivery device(s) in combination with the audio cue arrangements.

5. An interactive gaming system according to claim 1 further comprising a visual display screen that is driven by the game machine to present visual information relating to the game scenario, and wherein the game machine is configured to display information indicative of the user's performance in the game scenario on the visual display screen.

6. An interactive gaming system according to claim 1 wherein the game machine is configured to customize the audio cue arrangements of the game scenario to the user based on a user tinnitus profile that defines one or more assessed tinnitus sound characteristics of the user.

7. An interactive gaming system according to claim 6 wherein the user tinnitus profile is in the form of a stored electronic data file that is retrieved from an associated data storage medium by the game machine.

8. An interactive gaming system according to claim 6 wherein the game machine is configured to run an initial user calibration function prior to commencing game play of a game scenario to re-assess the user's perceived tinnitus sound characteristic relative to those stored in the user tinnitus profile and the user calibration function generating calibration data indicative of the user's current perceived tinnitus sound characteristics, wherein the game machine is configured to customize the audio cue arrangements of the game scenario based at least partly on the user tinnitus profile and calibration data.

9. An interactive gaming system according to claim 8 wherein the game machine is configured to store the calibration data and user game play performance data indicative of the user's game play performance in one or more electronic data files in an associated data storage medium at the end of a game play session of the game scenario.

10. An interactive gaming system according to claim 9 wherein the game machine is configured to retrieve previous user calibration data and game play performance data from the associated data storage medium and to configure the game scenario for the next game play session based at least partly on the retrieved data.

11. An interactive gaming system according to claim 1 wherein the game machine is configured to provide a game scenario arranged for audio training for tinnitus rehabilitation, and wherein the game scenario is configured to provide audio training according to any one or more of the following: sound localization training, frequency discrimination training, frequency categorization training, attention training, tone pips stimulation on broad frequency band.

12. An interactive gaming system according to claim 1 wherein the game scenario is configured to provide sound localization training and wherein the audio cue arrangements of the game scenario comprise a combination of one or more distracter sound(s) having sound characteristics that substantially correspond to at least one characteristic of the tinnitus as perceived by the user and one or more target sound(s) having no such correspondence to the user's perceived tinnitus, and the game machine being configured to advance the user in the game scenario in response to user feedback via the user interface indicative of the user identifying the target sound(s).

13. An interactive gaming system according to claim 1 the game scenario is configured to provide categorization training (CT) and/or discrimination training (DT) and wherein the audio cue arrangements of the game scenario comprise a combination or one or more target sounds and one or more distractor sounds, the sound characteristics of each sound being configured based on one or more sound characteristics of the tinnitus as perceived by the user, and the game machine being configured to advance the user in the game scenario in response to user feedback via the user interface indicative of the user correctly categorizing target and distractor sounds or discriminating between the target and distractor sounds.

14. An interactive gaming system according to claim 13 wherein the game scenario is switchable between either a CT mode or a DT mode, and the sound characteristics of the target and distract or sounds are configured according to each mode of training.

15. An interactive auditory training rehabilitation gaming system for a user suffering tinnitus comprising:
an electronic game machine having a processor configured to provide a game scenario in which the user's performance in the game scenario is based on the user's response to audio cue arrangements comprising a combination of sounds, and where at least one of the sounds has one or more sound characteristics that are configured based on one or more sound characteristics of the user's perceived tinnitus;
an audio delivery device or devices that are driven by the game machine to present the audio cue arrangements to the user in accordance with the game scenario, and wherein the audio delivery devices comprise left and right ear-level audio delivery devices that are worn by the user; the audio cue arrangement(s) generated by the game machine are provided in the form of left and right audio signals that are converted to audible sound by their respective left and right ear-level audio delivery devices; and the left and right audio signals generate at least one sound having a virtual sound source location in 3D auditory space such that the sound appears to originate from a desired direction within the auditory space; and
a user interface in signal communication with the game machine and which is operable by a user to interact with the game scenario by responding to the audio cue arrangements.

16. An interactive gaming system according to claim 15 wherein the sound characteristics of the user's perceived tinnitus comprise any one or more of the following sound attributes: frequency, patch, bandwidth, loudness, temporal properties, or type of stimuli.

17. An interactive gaming system according to claim 15 wherein at least one audio cue arrangement comprises a sequential playback of sounds in accordance with a playback timeline.

18. An interactive gaming system according to claim 15 wherein the game machine is configured to present background noise or ambient sound constantly or intermittently over the audio delivery device(s) in combination with the audio cue arrangements.

19. An interactive gaming system according to claim 15 further comprising a visual display screen that is driven by the game machine to present visual information relating to the game scenario, and wherein the game machine is configured to display information indicative of the user's performance in the game scenario on the visual display screen.

20. An interactive gaming system according to claim 15 wherein the game machine is configured to customize the audio cue arrangements of the game scenario to the user based on a user tinnitus profile that defines one or more assessed tinnitus sound characteristics of the user.

21. An interactive gaming system according to claim 20 wherein the user tinnitus profile is in the form of a stored electronic data file that is retrieved from an associated data storage medium by the game machine.

22. An interactive gaming system according to claim 20 wherein the game machine is configured to run an initial user calibration function prior to commencing game play of a game scenario to re-assess the user's perceived tinnitus sound characteristic relative to those stored in the user tinnitus profile and the user calibration function generating calibration data indicative of the user's current perceived tinnitus sound characteristics, wherein the game machine is configured to customize the audio cue arrangements of the game scenario based at least partly on the user tinnitus profile and calibration data.

23. An interactive gaming system according to claim 22 wherein the game machine is configured to store the calibration data and user game play performance data indicative of the user's game play performance in one or more electronic data files in an associated data storage medium at the end of a game play session of the game scenario.

24. An interactive gaming system according to claim 23 wherein the game machine is configured to retrieve previous user calibration data and game play performance data from the associated data storage medium and to configure the game scenario for the next game play session based at least partly on the retrieved data.

25. An interactive gaming system according to claim 15 wherein the game machine is configured to provide a game scenario arranged for audio training for tinnitus rehabilitation, and wherein the game scenario is configured to provide audio training according to any one or more of the following: sound localization training, frequency discrimination training, frequency categorization training, attention training, tone pips stimulation on broad frequency band.

26. An interactive gaming system according to claim 15 wherein the game scenario is configured to provide sound localization training and wherein the audio cue arrangements of the game scenario comprise a combination of one or more distracter sound(s) having sound characteristics that substantially correspond to at least one characteristic of the tinnitus as perceived by the user and one or more target sound(s) having no such correspondence to the user's perceived tinnitus, and the game machine being configured to advance the user in the game scenario in response to user feedback via the user interface indicative of the user identifying the target sound(s).

27. An interactive gaming system according to claim 15 the game scenario is configured to provide categorization training (CT) and/or discrimination training (DT) and wherein the audio cue arrangements of the game scenario comprise a combination or one or more target sounds and one or more distractor sounds, the sound characteristics of each sound being configured based on one or more sound characteristics of the tinnitus as perceived by the user, and the game machine being configured to advance the user in the game scenario in response to user feedback via the user interface indicative of the user correctly categorizing target and distractor sounds or discriminating between the target and distractor sounds.

28. An interactive gaming system according to claim 27 wherein the game scenario is switchable between either a CT mode or a DT mode, and the sound characteristics of the target and distractor sounds are configured according to each mode of training.

29. An interactive auditory training rehabilitation gaming system for a user suffering tinnitus comprising:

an electronic game machine having a processor configured to provide a game scenario in which the user's performance in the game scenario is based on the user's response to audio cue arrangements comprising a combination of sounds, wherein the game scenario has multiple game levels, and each level comprises one or more audio cue arrangements that may be selectively presented to the user for interaction, and where at least one of the sounds has one or more sound characteristics that are configured based on one or more sound characteristics of the user's perceived tinnitus;

an audio delivery device or devices that are driven by the game machine to present the audio cue arrangements to the user in accordance with the game scenario; and a user interface in signal communication with the game machine and which is operable by a user to interact with the game scenario by responding to the audio cue arrangements.

30. An interactive gaming system according to claim 29 wherein the sound characteristics of the user's perceived tinnitus comprise any one or more of the following sound attributes: frequency, patch, bandwidth, loudness, temporal properties, or type of stimuli.

31. An interactive gaming system according to claim 29, wherein the sound characteristics of the user's perceived tinnitus comprises spatial attributes indicative of the spatial location in 3D auditory space of the sound source location of the tinnitus as perceived by the user.

32. An interactive gaming system according to claim 29, wherein:
the audio delivery devices comprise left and right ear-level audio delivery devices that are worn by the user;
the audio cue arrangement(s) generated by the game machine are provided in the form of left and right audio signals that are converted to audible sound by their respective left and right ear-level audio delivery devices; and
the left and right audio signals generate at least one sound having a virtual sound source location in 3D auditory space such that the sound appears to originate from a desired direction within the auditory space.

33. An interactive gaming system according to claim 29 wherein at least one audio cue arrangement comprises a sequential playback of sounds in accordance with a playback timeline.

34. An interactive gaming system according to claim 29 wherein the game machine is configured to present background noise or ambient sound constantly or intermittently over the audio delivery device(s) in combination with the audio cue arrangements.

35. An interactive gaming system according to claim 29 further comprising a visual display screen that is driven by the game machine to present visual information relating to the game scenario, and wherein the game machine is configured to display information indicative of the user's performance in the game scenario on the visual display screen.

36. An interactive gaming system according to claim 29 wherein the game machine is configured to customize the audio cue arrangements of the game scenario to the user based on a user tinnitus profile that defines one or more assessed tinnitus sound characteristics of the user.

37. An interactive gaming system according to claim 36 wherein the user tinnitus profile is in the form of a stored electronic data file that is retrieved from an associated data storage medium by the game machine.

38. An interactive gaming system according to claim 36 wherein the game machine is configured to run an initial user calibration function prior to commencing game play of a game scenario to re-assess the user's perceived tinnitus sound characteristic relative to those stored in the user tinnitus profile and the user calibration function generating calibration data indicative of the user's current perceived tinnitus sound characteristics, wherein the game machine is configured to customize the audio cue arrangements of the game scenario based at least partly on the user tinnitus profile and calibration data.

39. An interactive gaming system according to claim 38 wherein the game machine is configured to store the calibration data and user game play performance data indicative of the user's game play performance in one or more electronic data files in an associated data storage medium at the end of a game play session of the game scenario.

40. An interactive gaming system according to claim 39 wherein the game machine is configured to retrieve previous user calibration data and game play performance data from the associated data storage medium and to configure the game scenario for the next game play session based at least partly on the retrieved data.

41. An interactive gaming system according to claim 29 wherein the game machine is configured to provide a game scenario arranged for audio training for tinnitus rehabilitation, and wherein the game scenario is configured to provide audio training according to any one or more of the following: sound localization training, frequency discrimination training, frequency categorization training, attention training, tone pips stimulation on broad frequency band.

42. An interactive auditory training rehabilitation gaming system for a user suffering tinnitus comprising:
an electronic game machine having a processor configured to provide a game scenario in which the user's performance in the game scenario is based on the user's response to audio cue arrangements comprising a combination of sounds, and where at least one of the sounds has one or more sound characteristics that are configured based on one or more sound characteristics of the user's perceived tinnitus, wherein the game machine is further configured to generate at least one audio cue arrangement dynamically in real-time during game play based at least partly on user interaction via the user interface;
an audio delivery device or devices that are driven by the game machine to present the audio cue arrangements to the user in accordance with the game scenario; and
a user interface in signal communication with the game machine and which is operable by a user to interact with the game scenario by responding to the audio cue arrangements.

43. An interactive gaming system according to claim 42 wherein the sound characteristics of the user's perceived tinnitus comprise any one or more of the following sound attributes: frequency, patch, bandwidth, loudness, temporal properties, or type of stimuli.

44. An interactive gaming system according to claim 42, wherein the sound characteristics of the user's perceived tinnitus comprises spatial attributes indicative of the spatial location in 3D auditory space of the sound source location of the tinnitus as perceived by the user.

45. An interactive gaming system according to claim 42, wherein:
the audio delivery devices comprise left and right ear-level audio delivery devices that are worn by the user;
the audio cue arrangement(s) generated by the game machine are provided in the form of left and right audio signals that are converted to audible sound by their respective left and right ear-level audio delivery devices; and
the left and right audio signals generate at least one sound having a virtual sound source location in 3D auditory space such that the sound appears to originate from a desired direction within the auditory space.

46. An interactive gaming system according to claim 42 the game scenario has multiple game levels, and each level comprises one or more audio cue arrangements that may be selectively presented to the user for interaction.

47. An interactive gaming system according to claim 42 wherein at least one audio cue arrangement comprises a sequential playback of sounds in accordance with a playback timeline.

48. An interactive gaming system according to claim 42 wherein the game machine is configured to present background noise or ambient sound constantly or intermittently over the audio delivery device(s) in combination with the audio cue arrangements.

49. An interactive gaming system according to claim 42 further comprising a visual display screen that is driven by the game machine to present visual information relating to the game scenario, and wherein the game machine is configured to display information indicative of the user's performance in the game scenario on the visual display screen.

50. An interactive gaming system according to claim 42 wherein the game machine is configured to customize the audio cue arrangements of the game scenario to the user based on a user tinnitus profile that defines one or more assessed tinnitus sound characteristics of the user.

51. An interactive gaming system according to claim 50 wherein the user tinnitus profile is in the form of a stored electronic data file that is retrieved from an associated data storage medium by the game machine.

52. An interactive gaming system according to claim 50 wherein the game machine is configured to run an initial user calibration function prior to commencing game play of a game scenario to re-assess the user's perceived tinnitus sound characteristic relative to those stored in the user tinnitus profile and the user calibration function generating calibration data indicative of the user's current perceived tinnitus sound characteristics, wherein the game machine is configured to customize the audio cue arrangements of the game scenario based at least partly on the user tinnitus profile and calibration data.

53. An interactive gaming system according to claim 52 wherein the game machine is configured to store the calibration data and user game play performance data indicative of the user's game play performance in one or more electronic data files in an associated data storage medium at the end of a game play session of the game scenario.

54. An interactive gaming system according to claim 53 wherein the game machine is configured to retrieve previous user calibration data and game play performance data from the associated data storage medium and to configure the game scenario for the next game play session based at least partly on the retrieved data.

55. An interactive gaming system according to claim 42 wherein the game machine is configured to provide a game scenario arranged for audio training for tinnitus rehabilitation, and wherein the game scenario is configured to provide audio training according to any one or more of the following: sound localization training, frequency discrimination training, frequency categorization training, attention training, tone pips stimulation on broad frequency band.

* * * * *